US009072317B2

(12) United States Patent
Minvielle

(10) Patent No.: US 9,072,317 B2
(45) Date of Patent: *Jul. 7, 2015

(54) TRANSFORMATION SYSTEM FOR NUTRITIONAL SUBSTANCES

(71) Applicant: Eugenio Minvielle, Rye, NY (US)

(72) Inventor: Eugenio Minvielle, Rye, NY (US)

( * ) Notice: Subject to any disclaimer, the term of this patent is extended or adjusted under 35 U.S.C. 154(b) by 47 days.

This patent is subject to a terminal disclaimer.

(21) Appl. No.: 13/921,078

(22) Filed: Jun. 18, 2013

(65) Prior Publication Data

US 2013/0276644 A1    Oct. 24, 2013

Related U.S. Application Data

(63) Continuation-in-part of application No. 13/560,965, filed on Jul. 27, 2012, now Pat. No. 8,490,862, which is a continuation of application No. 13/485,863, filed on May 31, 2012.

(60) Provisional application No. 61/625,002, filed on Apr. 16, 2012, provisional application No. 61/625,010, filed on Apr. 16, 2012.

(51) Int. Cl.
*G06F 17/00* (2006.01)
*A23P 1/00* (2006.01)
(Continued)

(52) U.S. Cl.
CPC ............... *A23P 1/00* (2013.01); *G09B 19/0092* (2013.01); *G06Q 30/0283* (2013.01); *A23L 3/00* (2013.01); *A23L 1/00* (2013.01); *G09B 19/00* (2013.01); *G06F 19/3475* (2013.01)

(58) Field of Classification Search
CPC .................... A23V 2002/00; A23V 2250/156; A61K 2300/00; G06F 19/3475; G06F 19/3406; G06F 19/3418; G06F 15/025; G06F 19/22; G06F 19/28; G06F 19/321; G06F 19/324; G06F 19/328; G06F 19/345; G06F 19/3456
USPC ............................... 235/375, 383, 492, 382.5
See application file for complete search history.

(56) References Cited

U.S. PATENT DOCUMENTS 4,225,410 A    9/1980  Pace
4,555,930 A   12/1985  Leach et al.
(Continued)

FOREIGN PATENT DOCUMENTS

DE    10 2005 040206 A1    2/2007
EP          1117055 A2     7/2001
(Continued)

OTHER PUBLICATIONS

Etherington, Darrell, "iCarte Turns the iPhone Into an RFID Reader," Gigaom, Nov. 18, 2009 (downloaded Oct. 3, 2013, from URL http://gigaom.com/2009/11/18/icarte-turns-the-iphone-into-an-rfid-reader/).

(Continued)

*Primary Examiner* — Thien M Le
(74) *Attorney, Agent, or Firm* — Nixon Peabody LLP

(57) ABSTRACT

Disclosed herein is a transformation system for at least one component of a single or multi-component nutritional substance. The transformation system obtains information regarding the nutritional substance to be transformed, the desired transformation, and the desired properties, including nutritional content, of the transformed nutritional substance, and dynamically modifies the transformation in response to this information.

30 Claims, 6 Drawing Sheets

Nutritional Substance Supply System 10

(51) Int. Cl.
*G09B 19/00* (2006.01)
*G06Q 30/02* (2012.01)
*A23L 3/00* (2006.01)
*A23L 1/00* (2006.01)
*G06F 19/00* (2011.01)

(56) References Cited

U.S. PATENT DOCUMENTS

| | | |
|---|---|---|
| 4,644,154 A | 2/1987 | Brogardh et al. |
| 4,650,766 A | 3/1987 | Harm et al. |
| 4,674,320 A | 6/1987 | Hirschfeld |
| D333,782 S | 3/1993 | van Berlo |
| 5,250,789 A | 10/1993 | Johnsen |
| 5,412,560 A | 5/1995 | Dennison |
| 5,442,669 A | 8/1995 | Medin |
| 5,478,900 A | 12/1995 | Amano et al. |
| 5,478,989 A | 12/1995 | Shepley |
| 5,478,990 A | 12/1995 | Montanari et al. |
| 5,673,691 A | 10/1997 | Abrams et al. |
| 5,697,177 A | 12/1997 | Ludlow et al. |
| 5,804,803 A | 9/1998 | Cragun et al. |
| 5,853,790 A | 12/1998 | Glancy |
| 5,872,721 A | 2/1999 | Huston et al. |
| 5,954,640 A | 9/1999 | Szabo |
| 6,012,415 A | 1/2000 | Linseth |
| 6,119,531 A | 9/2000 | Wendte et al. |
| 6,182,725 B1 | 2/2001 | Sorvik |
| 6,211,789 B1 | 4/2001 | Oldham et al. |
| 6,270,724 B1 | 8/2001 | Woodaman |
| 6,276,264 B1 | 8/2001 | Dumm |
| 6,310,964 B1 | 10/2001 | Mohan et al. |
| 6,325,878 B1 | 12/2001 | Borgstrom |
| 6,356,940 B1 | 3/2002 | Short |
| 6,387,049 B1 | 5/2002 | Moore |
| 6,444,233 B1 | 9/2002 | Arntzen et al. |
| 6,483,434 B1 | 11/2002 | Umiker |
| 6,491,217 B2 | 12/2002 | Catan |
| 6,502,411 B2 | 1/2003 | Okamoto |
| 6,512,919 B2 | 1/2003 | Ogasawara |
| 6,513,532 B2 | 2/2003 | Mault et al. |
| 6,538,215 B2 | 3/2003 | Montagnino et al. |
| 6,549,818 B1 | 4/2003 | Ali |
| 6,553,386 B1 | 4/2003 | Alabaster |
| 6,554,182 B1 | 4/2003 | Magnusson et al. |
| 6,556,963 B1 | 4/2003 | Tetzlaff |
| 6,571,603 B1 | 6/2003 | Doleman et al. |
| D478,773 S | 8/2003 | Palen |
| 6,616,047 B2 | 9/2003 | Catan |
| 6,631,333 B1 | 10/2003 | Lewis et al. |
| 6,671,698 B2 | 12/2003 | Pickett et al. |
| 6,676,014 B2 | 1/2004 | Catan |
| 6,689,398 B2 | 2/2004 | Haridas et al. |
| 6,691,135 B2 | 2/2004 | Pickett et al. |
| 6,716,462 B2 | 4/2004 | Prosise et al. |
| 6,773,926 B1 | 8/2004 | Freund et al. |
| 6,789,021 B2 | 9/2004 | Rendahl et al. |
| 6,844,197 B1 | 1/2005 | Doleman et al. |
| 6,874,000 B2 | 3/2005 | Sholl et al. |
| 6,888,458 B2 | 5/2005 | Carlson |
| 6,953,342 B2 | 10/2005 | Bisogno |
| 6,975,910 B1 | 12/2005 | Brown et al. |
| 6,982,640 B2 | 1/2006 | Lindsay et al. |
| 7,024,369 B1 | 4/2006 | Brown et al. |
| 7,076,438 B1 | 7/2006 | Tobelmann et al. |
| 7,085,777 B2 | 8/2006 | Beck et al. |
| 7,090,638 B2 | 8/2006 | Vidgen |
| 7,103,481 B2 | 9/2006 | Negri |
| 7,151,447 B1 | 12/2006 | Willms et al. |
| 7,152,040 B1 | 12/2006 | Hawthorne et al. |
| D534,758 S | 1/2007 | Lee et al. |
| D539,072 S | 3/2007 | Kawata et al. |
| D539,595 S | 4/2007 | Okuda et al. |
| D540,613 S | 4/2007 | Jeon |
| D541,578 S | 5/2007 | Jeon |
| 7,212,955 B2 | 5/2007 | Kirshenbaum et al. |
| 7,213,743 B2 | 5/2007 | Carlson et al. |
| 7,215,420 B2 | 5/2007 | Gellerman et al. |
| 7,237,400 B2 | 7/2007 | Owada |
| 7,256,699 B2 | 8/2007 | Tethrake et al. |
| 7,275,863 B1 | 10/2007 | Akers et al. |
| 7,295,889 B2 | 11/2007 | Lahteenmaki |
| D560,960 S | 2/2008 | Hillmann et al. |
| 7,357,316 B2 | 4/2008 | Heckel et al. |
| 7,359,802 B1 | 4/2008 | Lewis et al. |
| 7,372,003 B2 | 5/2008 | Kates |
| 7,396,550 B2 | 7/2008 | Angel |
| 7,403,855 B2 | 7/2008 | Fuessley et al. |
| 7,440,901 B1 | 10/2008 | Dlott et al. |
| 7,474,965 B2 | 1/2009 | Johnson et al. |
| 7,571,676 B2 | 8/2009 | Nelson et al. |
| 7,620,531 B1 | 11/2009 | Johnson |
| D607,264 S | 1/2010 | Lee |
| 7,681,383 B2 | 3/2010 | Argetsinger et al. |
| D618,488 S | 6/2010 | Knochner |
| 7,743,591 B2 | 6/2010 | Meier et al. |
| 7,797,204 B2 | 9/2010 | Balent |
| 7,836,876 B2 | 11/2010 | Schellenberg |
| 7,840,359 B2 | 11/2010 | Hsiung et al. |
| 7,854,108 B2 | 12/2010 | Koselka et al. |
| D633,326 S | 3/2011 | Shin et al. |
| 7,951,079 B1 | 5/2011 | Moore |
| 7,957,850 B2 | 6/2011 | Anderson |
| 7,996,134 B2 | 8/2011 | Roberts |
| 8,009,048 B2 | 8/2011 | Hyde et al. |
| 8,033,237 B2 | 10/2011 | Havens et al. |
| 8,082,809 B2 | 12/2011 | Luellen et al. |
| D654,299 S | 2/2012 | Benold |
| 8,112,303 B2 | 2/2012 | Eglen et al. |
| D657,607 S | 4/2012 | Ohmae et al. |
| 8,193,474 B2 | 6/2012 | Harris |
| D665,220 S | 8/2012 | Ohmae et al. |
| 8,285,593 B2 | 10/2012 | Bhatt et al. |
| 8,314,701 B2 | 11/2012 | Grieco et al. |
| D673,001 S | 12/2012 | Becze et al. |
| 8,393,137 B1 | 3/2013 | Crosby |
| 8,403,215 B2 | 3/2013 | Aihara et al. |
| 8,490,862 B1 * | 7/2013 | Minvielle ............ 235/375 |
| 8,550,365 B1 | 10/2013 | Minvielle |
| 8,626,796 B2 | 1/2014 | McBride et al. |
| 8,631,050 B1 | 1/2014 | Gayle |
| 8,668,140 B2 | 3/2014 | Minvielle |
| D702,482 S | 4/2014 | Davis et al. |
| 8,733,631 B2 | 5/2014 | Minvielle |
| 8,783,556 B2 | 7/2014 | Minvielle |
| 8,796,510 B2 * | 8/2014 | Heard et al. ............ 800/298 |
| 8,851,365 B2 | 10/2014 | Minvielle |
| 9,016,193 B2 | 4/2015 | Minvielle |
| 2002/0004749 A1 | 1/2002 | Froseth et al. |
| 2002/0011567 A1 | 1/2002 | Ozanich |
| 2002/0040564 A1 | 4/2002 | Killingbeck et al. |
| 2002/0059175 A1 | 5/2002 | Nakano |
| 2002/0091593 A1 | 7/2002 | Fowler |
| 2002/0106432 A1 | 8/2002 | Yamagata et al. |
| 2002/0125313 A1 | 9/2002 | Broff |
| 2002/0168456 A1 | 11/2002 | Robbins |
| 2003/0006281 A1 | 1/2003 | Thomas et al. |
| 2003/0027161 A1 | 2/2003 | Bejanin et al. |
| 2003/0099157 A1 | 5/2003 | Quine |
| 2003/0136960 A1 | 7/2003 | Goodman et al. |
| 2003/0163354 A1 | 8/2003 | Shamoun |
| 2003/0165602 A1 | 9/2003 | Garwood |
| 2003/0185937 A1 | 10/2003 | Garwood |
| 2003/0185948 A1 | 10/2003 | Garwood |
| 2003/0227392 A1 | 12/2003 | Ebert et al. |
| 2004/0045202 A1 | 3/2004 | Arrendale, III et al. |
| 2004/0083201 A1 | 4/2004 | Sholl et al. |
| 2004/0100380 A1 | 5/2004 | Lindsay et al. |
| 2004/0130714 A1 | 7/2004 | Gellerman et al. |
| 2004/0147038 A1 | 7/2004 | Lewis et al. |
| 2004/0152131 A1 | 8/2004 | Hsieh |
| 2004/0167724 A1 | 8/2004 | Federer et al. |
| 2004/0191382 A1 | 9/2004 | Cooper et al. |
| 2004/0201454 A1 | 10/2004 | Waterhouse et al. |
| 2004/0215402 A1 | 10/2004 | Hsiung et al. |

(56) References Cited

U.S. PATENT DOCUMENTS

| | | |
|---|---|---|
| 2004/0267098 A1 | 12/2004 | Moore |
| 2005/0001728 A1 | 1/2005 | Appelt et al. |
| 2005/0027726 A1 | 2/2005 | Guivarch et al. |
| 2005/0049920 A1 | 3/2005 | Day et al. |
| 2005/0075900 A1 | 4/2005 | Arguimbau, III |
| 2005/0079491 A1 | 4/2005 | Donne-Gousse et al. |
| 2005/0168325 A1 | 8/2005 | Lievre et al. |
| 2005/0171738 A1 | 8/2005 | Kadaba |
| 2005/0247213 A1 | 11/2005 | Slilaty |
| 2005/0248455 A1 | 11/2005 | Pope et al. |
| 2005/0251449 A1 | 11/2005 | Pape et al. |
| 2006/0015371 A1 | 1/2006 | Knauf et al. |
| 2006/0061454 A1 | 3/2006 | Debord et al. |
| 2006/0062835 A1 | 3/2006 | Weil |
| 2006/0073483 A1 | 4/2006 | White et al. |
| 2006/0078658 A1 | 4/2006 | Owens et al. |
| 2006/0099310 A1 | 5/2006 | Koekkoek |
| 2006/0130498 A1 | 6/2006 | Joshi et al. |
| 2006/0172048 A1 | 8/2006 | Etchells et al. |
| 2006/0178841 A1 | 8/2006 | Fernandez |
| 2006/0200480 A1 | 9/2006 | Harris et al. |
| 2006/0228428 A1* | 10/2006 | Kang et al. ............ 424/725 |
| 2006/0240174 A1 | 10/2006 | Jung et al. |
| 2006/0256132 A1 | 11/2006 | Shin et al. |
| 2006/0277064 A1 | 12/2006 | Cannata |
| 2006/0286211 A1 | 12/2006 | Lang |
| 2007/0016852 A1 | 1/2007 | Kim et al. |
| 2007/0036840 A1* | 2/2007 | Tuduri et al. ............ 424/442 |
| 2007/0055551 A1 | 3/2007 | Szabo |
| 2007/0055573 A1 | 3/2007 | Grell |
| 2007/0059402 A1 | 3/2007 | Barmore |
| 2007/0118394 A1 | 5/2007 | Cahoon |
| 2007/0191689 A1 | 8/2007 | Elitok |
| 2007/0209656 A1 | 9/2007 | Lee |
| 2007/0258048 A1 | 11/2007 | Pitchers |
| 2007/0269557 A1 | 11/2007 | Culver et al. |
| 2007/0294129 A1 | 12/2007 | Froseth et al. |
| 2007/0298147 A1 | 12/2007 | Haus |
| 2008/0058783 A1 | 3/2008 | Altshuler et al. |
| 2008/0059342 A1 | 3/2008 | Culver et al. |
| 2008/0077455 A1 | 3/2008 | Gilboa |
| 2008/0083825 A1 | 4/2008 | Yang et al. |
| 2008/0091705 A1 | 4/2008 | McBride et al. |
| 2008/0158543 A1 | 7/2008 | Puskas et al. |
| 2008/0171120 A1 | 7/2008 | Willett |
| 2008/0183588 A1 | 7/2008 | Agrawal et al. |
| 2008/0186175 A1 | 8/2008 | Stern |
| 2008/0195456 A1 | 8/2008 | Fitzpatrick et al. |
| 2008/0254449 A1 | 10/2008 | Plante |
| 2008/0275309 A1 | 11/2008 | Stivoric et al. |
| 2009/0029014 A1 | 1/2009 | Walter et al. |
| 2009/0065570 A1 | 3/2009 | Peters et al. |
| 2009/0070040 A1 | 3/2009 | Rabinovitch et al. |
| 2009/0099873 A1 | 4/2009 | Kurple |
| 2009/0157460 A1 | 6/2009 | Narayanaswamy |
| 2009/0177068 A1 | 7/2009 | Stivoric et al. |
| 2009/0202700 A1 | 8/2009 | Bunke et al. |
| 2009/0208607 A1 | 8/2009 | Bunke et al. |
| 2009/0232958 A1* | 9/2009 | Samoto et al. ............ 426/634 |
| 2009/0275002 A1 | 11/2009 | Hoggle |
| 2009/0276912 A1* | 11/2009 | Sherman et al. ............ 800/264 |
| 2009/0278685 A1 | 11/2009 | Potyrailo et al. |
| 2009/0282004 A1 | 11/2009 | Williams |
| 2009/0283517 A1 | 11/2009 | Mackay et al. |
| 2009/0286212 A1 | 11/2009 | Gordon |
| 2009/0288606 A1 | 11/2009 | Zimmerman |
| 2010/0055653 A1 | 3/2010 | Miller-Kovach et al. |
| 2010/0076585 A1 | 3/2010 | Mayer et al. |
| 2010/0097193 A1 | 4/2010 | Tang |
| 2010/0102959 A1 | 4/2010 | Ashrafzadeh et al. |
| 2010/0106625 A1 | 4/2010 | McCoy |
| 2010/0106626 A1 | 4/2010 | Ashrafzadeh et al. |
| 2010/0117819 A1 | 5/2010 | Murray |
| 2010/0119659 A1 | 5/2010 | Ovadia et al. |
| 2010/0135211 A1 | 6/2010 | Park et al. |
| 2010/0152687 A1 | 6/2010 | Carlozzi |
| 2010/0175886 A1* | 7/2010 | Bohacs et al. ............ 166/369 |
| 2010/0198605 A1 | 8/2010 | Saulet |
| 2010/0216098 A1 | 8/2010 | Montgomery |
| 2010/0216136 A1 | 8/2010 | B.Che Man et al. |
| 2010/0218044 A1 | 8/2010 | Roblett et al. |
| 2010/0228160 A1 | 9/2010 | Schweizer |
| 2010/0268658 A1 | 10/2010 | Medo et al. |
| 2010/0280895 A1 | 11/2010 | Mottola |
| 2010/0287101 A1 | 11/2010 | Ishikawa et al. |
| 2011/0029364 A1 | 2/2011 | Roeding et al. |
| 2011/0082711 A1 | 4/2011 | Poeze et al. |
| 2011/0124096 A1 | 5/2011 | Philipak et al. |
| 2011/0197827 A1 | 8/2011 | Chang |
| 2011/0204137 A1 | 8/2011 | Scharfenort et al. |
| 2011/0217205 A1 | 9/2011 | Peeters |
| 2011/0236862 A1 | 9/2011 | Culver et al. |
| 2011/0258130 A1 | 10/2011 | Grabiner et al. |
| 2011/0259960 A1 | 10/2011 | Baarman et al. |
| 2011/0301441 A1 | 12/2011 | Bandic et al. |
| 2011/0302050 A1 | 12/2011 | Kildevaeld |
| 2011/0318717 A1 | 12/2011 | Adamowicz |
| 2012/0004935 A1 | 1/2012 | Winkler |
| 2012/0005105 A1 | 1/2012 | Beier et al. |
| 2012/0009550 A1 | 1/2012 | Gayle |
| 2012/0016814 A1 | 1/2012 | Evans |
| 2012/0027897 A1 | 2/2012 | Innocenzi |
| 2012/0052162 A1 | 3/2012 | Goulart |
| 2012/0055718 A1 | 3/2012 | Chen |
| 2012/0083669 A1 | 4/2012 | Abujbara |
| 2012/0085828 A1 | 4/2012 | Ziegler |
| 2012/0085829 A1 | 4/2012 | Ziegler |
| 2012/0105424 A1 | 5/2012 | Lee et al. |
| 2012/0135455 A1* | 5/2012 | Nerin De La Puerta et al. ............ 435/34 |
| 2012/0169469 A1 | 7/2012 | Butler et al. |
| 2012/0173269 A1 | 7/2012 | Omidi |
| 2012/0179665 A1 | 7/2012 | Baarman et al. |
| 2012/0199643 A1 | 8/2012 | Minnick et al. |
| 2012/0203572 A1 | 8/2012 | Christensen |
| 2012/0216911 A1 | 8/2012 | Bartholomew et al. |
| 2012/0251663 A1 | 10/2012 | Prins et al. |
| 2012/0274470 A1 | 11/2012 | Sandvick |
| 2012/0290051 A1 | 11/2012 | Boyden et al. |
| 2012/0315609 A1 | 12/2012 | Miller-Kovach et al. |
| 2012/0321759 A1 | 12/2012 | Marinkovich et al. |
| 2013/0033031 A1 | 2/2013 | Key |
| 2013/0048736 A1 | 2/2013 | Wien |
| 2013/0048737 A1 | 2/2013 | Baym et al. |
| 2013/0052616 A1 | 2/2013 | Silverstein et al. |
| 2013/0080784 A1 | 3/2013 | Oertli |
| 2013/0105565 A1 | 5/2013 | Kamprath |
| 2013/0117310 A1 | 5/2013 | Chai et al. |
| 2013/0209615 A1 | 8/2013 | Lee et al. |
| 2013/0231711 A1 | 9/2013 | Kaib |
| 2013/0269297 A1 | 10/2013 | Minvielle |
| 2013/0269454 A1 | 10/2013 | Minvielle |
| 2013/0269537 A1 | 10/2013 | Minvielle |
| 2013/0269538 A1 | 10/2013 | Minvielle |
| 2013/0269542 A1 | 10/2013 | Minvielle |
| 2013/0269543 A1 | 10/2013 | Minvielle |
| 2013/0269544 A1 | 10/2013 | Minvielle |
| 2013/0270337 A1 | 10/2013 | Minvielle |
| 2013/0273217 A1 | 10/2013 | Minvielle |
| 2013/0273222 A1 | 10/2013 | Minvielle |
| 2013/0273507 A1 | 10/2013 | Minvielle |
| 2013/0273509 A1 | 10/2013 | Mutti |
| 2013/0275037 A1 | 10/2013 | Minvielle |
| 2013/0275318 A1 | 10/2013 | Minvielle |
| 2013/0275342 A1 | 10/2013 | Minvielle |
| 2013/0275343 A1 | 10/2013 | Minvielle |
| 2013/0275370 A1 | 10/2013 | Minvielle |
| 2013/0275426 A1 | 10/2013 | Minvielle |
| 2013/0275439 A1 | 10/2013 | Minvielle |
| 2013/0275460 A1 | 10/2013 | Minvielle |
| 2013/0275477 A1 | 10/2013 | Minvielle |
| 2013/0290364 A1 | 10/2013 | Minvielle |
| 2013/0295532 A1 | 11/2013 | Minvielle |
| 2013/0297642 A1 | 11/2013 | Minvielle |

(56) References Cited

U.S. PATENT DOCUMENTS

| | | |
|---|---|---|
| 2013/0309138 A1 | 11/2013 | Minvielle |
| 2013/0309636 A1 | 11/2013 | Minvielle |
| 2013/0309637 A1 | 11/2013 | Minvielle |
| 2013/0310955 A1 | 11/2013 | Minvielle |
| 2013/0337516 A1 | 12/2013 | Herrema |
| 2014/0018636 A1 | 1/2014 | Contant et al. |
| 2014/0037805 A1 | 2/2014 | Minvielle |
| 2014/0038140 A1 | 2/2014 | Minvielle |
| 2014/0041532 A1 | 2/2014 | Minvielle |
| 2014/0041533 A1 | 2/2014 | Minvielle |
| 2014/0061296 A1 | 3/2014 | Minvielle |
| 2014/0069838 A1 | 3/2014 | Minvielle |
| 2014/0191025 A1 | 7/2014 | Minvielle |
| 2014/0214714 A1 | 7/2014 | Minvielle |
| 2014/0236359 A1 | 8/2014 | Minvielle |
| 2014/0290395 A1 | 10/2014 | Minvielle |
| 2014/0290396 A1 | 10/2014 | Minvielle |
| 2014/0364971 A1 | 12/2014 | Minvielle |
| 2014/0364972 A1 | 12/2014 | Minvielle |
| 2015/0012122 A1 | 1/2015 | Minvielle |
| 2015/0017252 A1 | 1/2015 | Garland et al. |
| 2015/0037764 A1 | 2/2015 | Minvielle |
| 2015/0051841 A1 | 2/2015 | Minvielle |
| 2015/0057773 A1 | 2/2015 | Minvielle |
| 2015/0100350 A1 | 4/2015 | Minvielle |
| 2015/0100462 A1 | 4/2015 | Minvielle |

FOREIGN PATENT DOCUMENTS

| | | |
|---|---|---|
| EP | 1 253 303 A1 | 10/2002 |
| FR | 2813683 A1 | 3/2002 |
| GB | 2312054 A | 10/1997 |
| WO | 91/13304 A1 | 9/1991 |
| WO | WO 02/06984 | 1/2002 |
| WO | 02/37375 A1 | 5/2002 |
| WO | WO 2007108906 A2 | 9/2007 |
| WO | WO 2008/054231 A1 | 5/2008 |
| WO | WO 2013/126579 A1 | 8/2013 |
| WO | WO 2013/134325 A1 | 9/2013 |
| WO | WO 2013/134544 A1 | 9/2013 |
| WO | WO 2013/142218 A1 | 9/2013 |
| WO | WO 2013/158571 A2 | 10/2013 |
| WO | WO 2013/158572 A2 | 10/2013 |
| WO | WO 2013/158576 A1 | 10/2013 |
| WO | WO 2013/176800 A1 | 11/2013 |
| WO | WO 2013/180925 A2 | 12/2013 |
| WO | WO 2014/168844 A2 | 10/2014 |
| WO | WO 2014/182566 A2 | 11/2014 |
| WO | WO 2014/210531 A2 | 12/2014 |
| WO | WO 2015/006351 A1 | 1/2015 |
| WO | WO 2015/013030 A1 | 1/2015 |
| WO | WO 2015/013031 A2 | 1/2015 |
| WO | WO 2015/069325 A1 | 5/2015 |
| WO | WO 2015/069950 A1 | 5/2015 |
| WO | WO 2015/073569 A1 | 5/2015 |

OTHER PUBLICATIONS

Ghasemi-Varnamkhasti, M. et al., "Biomimetic-based odor and taste sensing systems to food quality and safety characterization: An overview on basic principles and recent achievements", Journal of Food Engineering, vol. 100, pp. 377-387, May 2010.
Greenfield, H. et al., "Food composition data," FAO, 2003 ("FAO").
Perks, B., "Fighting Food Fraud with Science", Text Reproduced from Chemistry World, 2007, vol. 4 (9), pp. 48-52.
Preechaburana, Pakorn et al., "Surface Plasmon Resonance Chemical Sensing on Cell Phones", Angewandte Chemie International Edition, vol. 51, Issue 46, pp. 11585-11588, first published online Oct. 16, 2012.
Notice of Allowance in U.S. Appl. No. 13/900,426, mailed Dec. 16, 2013.
Notice of Allowance in U.S. Appl. No. 13/931,744, mailed Feb. 28, 2014.
Notice of Allowance in U.S. Appl. No. 14/047,817, mailed Apr. 14, 2014.
Notice of Allowance in U.S. Appl. No. 14/074,664, mailed Jun. 2, 2014.
Office Action in U.S. Appl. No. 13/485,850, mailed Mar. 20, 2014.
Office Action in U.S. Appl. No. 13/485,850, mailed Sep. 30, 2013.
Office Action in U.S. Appl. No. 13/485,878, mailed Jun. 5, 2014.
Office Action in U.S. Appl. No. 13/485,878, mailed Oct. 24, 2013.
Office Action in U.S. Appl. No. 13/602,040, mailed Jul. 17, 2014.
Office Action in U.S. Appl. No. 13/602,040, mailed Oct. 23, 2013.
Office Action in U.S. Appl. No. 13/685,575, mailed Oct. 24, 2013.
Office Action in U.S. Appl. No. 13/732,050, mailed Apr. 10, 2014.
Office Action in U.S. Appl. No. 13/732,050, mailed Oct. 24, 2013.
Office Action in U.S. Appl. No. 13/771,004, mailed Apr. 4, 2014.
Office Action in U.S. Appl. No. 13/888,353, mailed Dec. 4, 2013 (restriction).
Office Action in U.S. Appl. No. 13/888,353, mailed Jul. 25, 2013 (restriction).
Office Action in U.S. Appl. No. 13/888,353, mailed May 1, 2014.
Office Action in U.S. Appl. No. 13/900,426, mailed Aug. 8, 2013.
Office Action in U.S. Appl. No. 13/931,744, mailed Aug. 20, 2013.
Office Action in U.S. Appl. No. 13/937,167, mailed Apr. 14, 2014.
Office Action in U.S. Appl. No. 13/937,167, mailed Oct. 28, 2013.
Office Action in U.S. Appl. No. 13/948,004, mailed Jun. 11, 2014.
Office Action in U.S. Appl. No. 13/948,004, mailed Oct. 24, 2013.
Office Action in U.S. Appl. No. 14/047,817, mailed Nov. 29, 2013.
Office Action in U.S. Appl. No. 14/059,441 mailed Jul. 10, 2014.
Office Action in U.S. Appl. No. 14/059,441, mailed Dec. 20, 2013.
Office Action in U.S. Appl. No. 14/059,441, mailed Feb. 11, 2014.
Office Action in U.S. Appl. No. 14/074,664, mailed Jan. 8, 2014.
Office Action in U.S. Appl. No. 14/137,963, mailed Aug. 5, 2014.
Restriction Requirement in U.S. Appl. No. 13/684,113, mailed Sep. 5, 2014.
Restriction Requirement in U.S. Appl. No. 14/137,963, mailed May 7, 2014.
Extended European Search Report in European Application No. 13731655.0, dated Feb. 24, 2014.
Extended European Search Report in European Application No. 13757669.0, dated Jan. 31, 2014.
Notice from the European Patent Office, dated Oct. 1, 2007, concerning business methods, Official Journal EPO, pp. 592-593.
International Search Report and Written Opinion in International Application No. PCT/US2013/36666, mailed Oct. 4, 2013.
International Search Report and Written Opinion in International Application No. PCT/US2013/036668, mailed Dec. 6, 2013.
International Search Report and Written Opinion in International Application No. PCT/US2013/036670, mailed Aug. 19, 2013.
International Search Report and Written Opinion in International Application No. PCT/US2013/036673, mailed Aug. 20, 2013.
International Search Report and Written Opinion in International Application No. PCT/US2013/040445, mailed Oct. 25, 2013.
Statement in accordance with the Notice from the European Patent Office, dated Oct. 1, 2007, concerning business methods.
Thakur, M. et al., "Food Traceability, R&D Norway", Food Technology, Apr. 2012, p. 42-46.
Hoffman, B., "IBM Announces Food Traceability Technology", Food+Tech Connect, Oct. 19, 2011, 2 pages.
"SIRA Technologies Food Sentinel System Thermal Barcode for Packaging", Sustainable is Good: Lifestyle and Design Blog, Mar. 4, 2009, 2 pages.
Montesinos, F., "Plant-associated Microorganisms: a View from the Scope of Microbiology", International Microbiology, Dec. 2003, vol. 6, Issue 4, pp. 221-223.
Sinclair, D.A. et al., "Unlocking the Secrets of Longevity Genes", Scientific American, Mar. 2006, vol. 294, Issue 3, pp. 48-57.
Diller, K.R., "Stress Protein Expression Kinetics", Annual Review of Biomedical Engineering, 2006, vol. 8, pp. 403-424.
Zerebecki, R.A. et al., "Temperature Tolerance and Stress Proteins as Mechanisms of Invasive Species Success", PLoS One, Apr. 2011, vol. 6, Issue 4, e14806, pp. 1-7.
Ni, Fu-Tai et al., "Gene Expression and Regulation of Higher Plants Under Soil Water Stress", Current Genomics, Jun. 2009, vol. 10, pp. 269-280.

(56) References Cited

OTHER PUBLICATIONS

Hayano-Kanashiro, C. et al., "Analysis of Gene Expression and Physiological Responses in Three Mexican Maize Landraces Under Drought Stress and Recovery Irrigation", PLoS One, Oct. 2009, vol. 4, Issue 10, e7531, pp. 1-19.
Kingsmore, S.F., "Multiplexed Protein Measurement: Technologies and Applications of Protein and Antibody Arrays", Nature Reviews Drug Discovery, Apr. 2006, vol. 5, pp. 310-321.
Kaume, L. et al., "The Blackberry Fruit: A Review on Its Composition and Chemistry, Metabolism and Bioavailability, and Health Benefits", Journal of Agricultural and Food Chemistry, 2012, vol. 60 (23), pp. 5716-5727.
Montealegre, C. et al., "Traceability Markers to the Botanical Origin in Olive Oils", Journal of Agricultural and Food Chemistry, 2010, vol. 58 (1), pp. 28-38.
Martins-Lopes, P. et al., "DNA Markers for Portuguese Olive Oil Fingerprinting", Journal of Agricultural and Food Chemistry, 2008, vol. 56 (24), pp. 11786-11791.
Garcia-Gonzalez, D.L. et al., "Research in Olive Oil: Challenges for the Near Future", Journal of Agricultural and Food Chemistry, 2010, vol. 58 (24), pp. 12569-12577.
Zou, Ming-Qiang et al., "Rapid Authentication of Olive Oil Adulteration by Raman Spectrometry", Journal of Agricultural and Food Chemistry, 2009, vol. 57 (14), pp. 6001-6006.
Frankel, E.N., "Chemistry of Extra Virgin Olive Oil: Adulteration, Oxidative Stability, and Antioxidants", Journal of Agricultural and Food Chemistry, 2010, vol. 58 (10), pp. 5991-6006.
Lago, Fatima C. et al., "FINS Methodology to Identification of Sardines and Related Species in Canned Products and Detection of Mixture by Means of SNP Analysis Systems", European Food Research and Technology, Jun. 2011, vol. 232(6), pp. 1077-1086.
Lago, Fatima C. et al., "Genetic Identification of Horse Mackerel and Related Species in Seafood Products by Means of Forensically Informative Nucleotide Sequencing Methodology", Journal of Agricultural and Food Chemistry, 2011, vol. 59 (6), pp. 2223-2228.
Suslick, B.A. et al., "Discrimination of Complex Mixtures by a Colorimetric Sensor Array: Coffee Aromas", Analytical Chemistry, Mar. 1, 2010, vol. 82, No. 5, pp. 2067-2073.
Rashidi, L. et al., "The Applications of Nanotechnology in Food Industry", Critical Reviews in Food Science and Nutrition, 2011, vol. 51, Issue 8, pp. 723-730.
Staggers, N. et al., "Nanotechnology: The Coming Revolution and its Implications for Consumers, Clinicians, and Informatics", Nursing Outlook, Sep.-Oct. 2008, vol. 56, No. 5, pp. 268-274.
Chaudhry, Q. et al., "Applications and Implications of Nanotechnologies for the Food Sector", Food Additives and Contaminants: Part A, Mar. 2008, vol. 25, Issue 3, pp. 241-258.
Srinivas, P.R. et al., "Nanotechnology Research: Applications in Nutritional Sciences", The Journal of Nutrition, Symposium-Nanotechnology Research: Applications in Nutritional Sciences, Jan. 2010, vol. 140, No. 1, pp. 119-124.
Walt, D.R., "Electronic Noses: Wake Up and Smell the Coffee", Analytical Chemistry, Feb. 1, 2005, vol. 77 (3), p. A-45.
Aernecke, M.J. et al., "Optical-fiber Arrays for Vapor Sensing", Sensors and Actuators B: Chemical, Nov. 2009, vol. 142, Issue 2, pp. 464-469.
Anslyn, E.V., "Supramolecular Analytical Chemistry", The Journal of Organic Chemistry, Feb. 2, 2007, vol. 72, No. 3, pp. 687-699.
Lewis, N.S., "Comparisons Between Mammalian and Artificial Olfaction Based on Arrays of Carbon Black-Polymer Composite Vapor Detectors", Accounts of Chemical Research, 2004, vol. 37, No. 9, pp. 663-672.
Rock, F. et al., "Electronic Nose: Current Status and Future Trends", Chemical Reviews, 2008, vol. 108, No. 2, pp. 705-725.
Hierlemann, A. et al., "Higher-Order Chemical Sensing", Chemical Reviews, 2008, vol. 108, No. 2, pp. 563-613.
Hsieh, Meng-Da et al., "Limits of Recognition for Simple Vapor Mixtures Determined with a Microsensor Array", Analytical Chemistry, Apr. 1, 2004, vol. 76, No. 7, pp. 1885-1895.
Grate, J.W., "Acoustic Wave Microsensor Arrays for Vapor Sensing", Chemical Reviews, 2000, vol. 100, No. 7, pp. 2627-2647.
Janata, J. et al., "Conducting Polymers in Electronic Chemical Sensors", Nature Materials, Jan. 2003, vol. 2, pp. 19-24.
Wolfbeis, O.5., "Materials for Fluorescence-based Optical Chemical Sensors", Journal of Materials Chemistry, 2005, vol. 15, pp. 2657-2669.
James, D. et al., "Chemical Sensors for Electronic Nose Systems", Microchimica Acta, Feb. 2005, vol. 149, pp. 1-17.
Primrose, S. et al., "Food Forensics: Methods for Determining the Authenticity of Foodstuffs", Trends in Food Science & Technology, Dec. 2010, vol. 21 (12), pp. 582-590.
Kharif, Olga, "Janne Haverinen: Mapping the Great Indoors", Bloomberg BusinessWeek, May 9, 2012, retrieved from URL: <http://www.businessweek.com/articles/2012-08-09/janne-haverinen-mapping-the-great-indoors on Apr. 12, 2013>.
Cheftel, J. Claude, "Food and Nutrition Labelling in the European Union", Food Chemistry 93.3, Dec. 2005, pp. 531-550, retrieved on Mar. 10, 2013 from URL: <http://www.sciencedirect.com/science/article/pii/S0308814604008581>.
U.S. Office Action in U.S. Appl. No. 13/485,850 mailed on May 9, 2013.
U.S. Office Action in U.S. Appl. No. 13/560,965 mailed on Feb. 1, 2013.
U.S. Office Action in U.S. Appl. No. 13/602,040 mailed on Jan. 11, 2013 (restriction).
U.S. Office Action in U.S. Appl. No. 13/685,575 mailed on May 6, 2013.
U.S. Office Action in U.S. Appl. No. 13/750,804 mailed on Mar. 12, 2013.
U.S. Office Action in U.S. Appl. No. 13/771,004 mailed on May 15, 2013.
Notice of Allowance in U.S. Appl. No. 13/560,965 mailed on Mar. 22, 2013.
Notice of Allowance in U.S. Appl. No. 13/750,804 mailed on May 31, 2013.
PCT International Search Report and Written Opinion in International Application No. PCT/US2013/029686, mailed on May 13, 2013.
PCT International Search Report and Written Opinion in International Application No. PCT/US2013/031106, mailed on May 31, 2013.
PCT International Search Report and Written Opinion in International Application No. PCT/US13/27148, mailed on Jun. 18, 2013.
PCT International Search Report and Written Opinion in International Application No. PCT/US13/29219, mailed on Jun. 20, 2013.
U.S. Office Action in U.S. Appl. No. 13/771,004 mailed on Jul. 8, 2013.
U.S. Office Action in U.S. Appl. No. 13/888,353 mailed on Jul. 25, 2013 (restriction).
Arora, P. et al., "An overview of transducers as platform for the rapid detection of foodborne pathogens", Appl. Microbial. Biotechnol., vol. 97, Issue 5, pp. 1829-1840, Jan. 18, 2013 (Published online).
"Automated Fruit Recognition" Fraunhofer, accessed online Nov. 13, 2014 and, available at http://www.iosb.fraunhofer.de/servlet/is/33328/.
Bell, S. et al., "Report on nutrient losses and gains factors used in European food composition databases", Technical Report, Apr. 2006, 66 pages (Retrieved from the Internet on Mar. 2, 2015 at: http://www.eurofir.net).
Chung, I-C. et al., "A Portable Electrochemical Sensor for Caffeine and (~)Epigallocatechin Gallate Based on Molecularly Imprinted Poly(ethylene-co-vinyl alcohol) Recognition Element", J Nanosci Nanotechnol., vol. 11, No. 12, Dec. 2011, pp. 10633-10638.
"Cool runnings needed for fine wines," AFP, Apr. 28, 2008, retrieved from internet URL http://www.google.com/hostednews/afp/article/ALeqM5hm5gRK3maWqEJppJOBObR71THV on Feb. 10, 2014.
Composition of Foods Raw, Processed, Prepared USDA National Nutrient Database for Standard Reference, Release 26 Documentation and User Guide, U.S. Department of Agriculture Agricultural Research Service, Aug. 2013 (revised Nov. 2013), 136 pages, accessed on its website, at http://www.ars.usda.gov/SP2UserFiles/Place/12354500/Data/SR26/sr26_doc.pdf.

(56) References Cited

OTHER PUBLICATIONS

De Vos, K. et al., "Multiplexed antibody detection with an array of silicon-on-insulator microring resonators", IEEE, Photonics Journal, vol. 1, Issue 4, Oct. 2009, pp. 225-235.
Dorokhin, D. et al., "Imaging surface plasmon resonance for multiplex microassay sensing of mycotoxins", Analytical and Bioanalytical Chemistry, vol. 400, Issue 9, published online Apr. 12, 2011, pp. 3005-3011.
Ebarvia, et al. "Biomimetic piezoelectric quartz sensor for caffeine based on a molecularly imprinted polymer", Analytical and Bioanalytical Chemistry, vol. 378, Issue 5, Mar. 2004, published online Jan. 27, 2004, pp. 1331-1337.
Focke, M. et al., "Lab-on-a-Foil: microfluidics on thin and flexible films", Lab on a Chip, vol. 10, Issue 11, published online Mar. 19, 2010, pp. 1365-1386.
Gartia, M. et al., "Colorimetric plasmon resonance imaging using nano lycurgus cup arrays", Advanced Optical Materials, vol. 1, Issue 1, Jan. 2013, pp. 68-76.
Huang, et al., "A passive radiofrequency pH sensing tag for wireless food quality monitoring", IEEE Sensors Journal, vol. 12, Issue 3, Mar. 2012, pp. 487-495.
Hugh, J. "Recipe Calculations: Where Do We Stand?", Proceedings of the 12th National Nutrient Databank Conference, Houston, Texas, Apr. 12, 1987, pp. 135-139 (Retrieved from the Internet on Feb. 13, 2015 at http://www.nutrientdataconf.org/PastConf/NDBC12/5-2_Joseph.pdf).
Kumar, A. et al., "Study of fiber optic sugar sensor", Pramana, vol. 67, Issue 2, Aug. 2006, pp. 383-387.
Kwon, H. et al., "Fluorescent DNAs printed on paper: Sensing food spoilage and ripening in the vapor phase", Chemical Science, vol. 3, Issue 8, published online May 17, 2012, pp. 2542-2549.
Lin, et al., "Multiplex fiber-optic biosensor using multiple particle plasmon resonances", International Society for Optics and Photonics: Third Asia Pacific Optical Sensors Conference, vol. 8351, Sydney, Australia, Jan. 31, 2012, pp. 83512S1-83512S7.
Ricci, F. et al., "A review on novel developments and applications of immunosensors in food analysis", Analytica Chimica Acta, vol. 605, Issue 2, Dec. 19, 2007, pp. 111-129.
Roche, PJR, et al., "A Camera Phone Localised Surface Plasmon Biosensing Platform Towards Low-Cost Label-Free Diagnostic Testing", Journal of Sensors, vol. 2011, 2011, 7 pages.
Scampicchio, M. et al., "Optical nanoprobes based on gold nanoparticles for sugar sensing", Nanotechnology, vol. 20, Issue 13, Apr. 1, 2009, 5 pages.
Valero, C., et al., "Design Guidelines for a Quality Assessment System of Fresh Fruits in Fruit Centers and Hypermarkets", Abstract, Agriculture Engineering International: the CIGR Journal of Scientific Research and Development, vol. II, Aug. 2000, 20 pages. Available online at http://dspace.library.cornell.edu/retrieve/237/, accessed Feb. 19, 2015.
Zhu, H. et al., "Quantum dot enabled detection of *Escherichia coli* using a cell-phone", Analyst, vol. 137, Issue 11, Jun. 7, 2012, pp. 2541-2544.
Office Action in U.S. Appl. No. 13/485,850, mailed Sep. 29, 2014.
Office Action in U.S. Appl. No. 13/485,863, mailed Feb. 9, 2015.
Advisory Action in U.S. Appl. No. 13/485,878, mailed Sep. 16, 2014.
Office Action in U.S. Appl. No. 13/485,883, mailed Feb. 3, 2015.
Office Action in U.S. Appl. No. 13/485,900, mailed Feb. 3, 2015.
Office Action in U.S. Appl. No. 13/685,575, mailed Oct. 27, 2014.
Office Action in U.S. Appl. No. 13/684,113, mailed Dec. 15, 2014.
Office Action in U.S. Appl. No. 13/729,548, mailed Dec. 2, 2014.
Office Action in U.S. Appl. No. 13/861,300 mailed Feb. 24, 2015.
Office Action in U.S. Appl. No. 13/888,353, mailed Oct. 1, 2014.
Office Action in U.S. Appl. No. 13/921,078, mailed Nov. 4, 2014.
Office Action in U.S. Appl. No. 13/931,733, mailed Nov. 6, 2014.
Office Action in U.S. Appl. No. 14/044,851, mailed Jan. 5, 2015.
Notice of Allowance in U.S. Appl. No. 14/059,441, mailed Jan. 5, 2015.
Notice of Allowance in U.S. Appl. No. 14/137,963, mailed Jan. 28, 2015.
Office Action in U.S. Appl. No. 14/304,671, mailed Feb. 4, 2015.
Office Action in U.S. Appl. No. 14,306,111, mailed Nov. 13, 2014.
Office Action in U.S. Appl. No. 29/497,888, mailed Nov. 19, 2014.
PCT International Search Report and Written Opinion in International Application No. PCT/US2014/044696, mailed Oct. 10, 2014.
PCT International Search Report and Written Opinion in International Application No. PCT/US2014/045796, mailed Oct. 15, 2014.
PCT International Search Report and Written Opinion in International Application No. PCT/US2014/045798, mailed Oct. 15, 2014.
PCT International Search Report and Written Opinion in International Application No. PCT/US2014/045807, mailed Jan. 22, 2015.
PCT International Search Report and Written Opinion in International Application No. PCT/US14/59186, mailed Dec. 22, 2014.
PCT International Search Report and Written Opinion in International Application No. PCT/US2014/064434, mailed Feb. 20, 2015.
Communication Pursuant to Article 94(3) in European Application No. 13731655.0, dated Jan. 22, 2015.
European Examination Report in European Application NO. 13757669.0, dated Oct. 13, 2014.
Extended European Search Report in European Application No. 13751912.0, dated Feb. 25, 2015.
PCT International Search Report and Written Opinion in International Application No. PCT/US2014/033084, mailed Mar. 6, 2015.
PCT International Search Report and Written Opinion in International Application No. PCT/US2014/036570, mailed Mar. 10, 2015.
PCT International Search Report and Written Opinion in International Application No. PCT/US2014/044700, mailed May 18, 2015.
PCT International Search Report and Written Opinion in International Application No. PCT/US2014/065281, mailed Mar. 13, 2015.
Office Action in U.S. Appl. No. 13/485,850, mailed Mar. 19, 2015.
Office Action in U.S. Appl. No. 13/485,866, mailed May 7, 2015.
Office Action in U.S. Appl. No. 13/485,883, mailed May 20, 2015.
Office Action in U.S. Appl. No. 13/485,916, mailed Mar. 27, 2015.
Office Action in U.S. Appl. No. 13/646,632, mailed Mar. 26, 2015.
Office Action in U.S. Appl. No. 13/685,575, mailed May 5, 2015.
Office Action in U.S. Appl. No. 13/771,004, mailed Mar. 10, 2015.
Office Action in U.S. Appl. No. 13/888,353, mailed Mar. 26, 2015.
Office Action in U.S. Appl. No. 13/931,733, mailed Mar. 10, 2015.
Notice of Allowance in U.S. Appl. No. 14/044,851, mailed Mar. 31, 2015.
Office Action in U.S. Appl. No. 14/203,353, mailed Mar. 31, 2015.
Office Action in U.S. Appl. No. 14/260,115, mailed Apr. 16, 2015.
Office Action in U.S. Appl. No. 14/466,805, mailed Apr. 13, 2015.
Office Action in U.S. Appl. No. 14/286,627, mailed Apr. 24, 2015.
Office Action in U.S. Appl. No. 14/466,824, mailed May 7, 2015.
Office Action in U.S. Appl. No. 14/467,433, mailed May 8, 2015.
Notice of Allowance in U.S. Appl. No. 14/306,111, mailed Mar. 17, 2015.

\* cited by examiner

| Consumer Attribute Criteria Input | "Listen To Your Food" Compliance Response Format | | | | | | | "Listen To Your Food" Non-compliance Response Format | | | | | | |
|---|---|---|---|---|---|---|---|---|---|---|---|---|---|---|
| | Visual | | Audio | | Other sensory | | | Visual | | Audio | | Other sensory | | |
| | Symbolic | Language | Symbolic | Language | Tactile | Thermal | Olfactory | Symbolic | Language | Symbolic | Language | Tactile | Thermal | Olfactory |
| Component attribute 1 | | | | | | | | | | | | | | |
| Component attribute 2 | | | | | | | | | | | | | | |
| Component attribute (n) | | | | | | | | | | | | | | |
| Integrity attribute 1 | | | | | | | | | | | | | | |
| Integrity attribute 2 | | | | | | | | | | | | | | |
| Integrity attribute (n) | | | | | | | | | | | | | | |
| Nutritional attribute 1 | | | | | | | | | | | | | | |
| Nutritional attribute 2 | | | | | | | | | | | | | | |
| Nutritional attribute (n) | | | | | | | | | | | | | | |
| Organoleptic attribute 1 | | | | | | | | | | | | | | |
| Organoleptic attribute 2 | | | | | | | | | | | | | | |
| Organoleptic attribute (n) | | | | | | | | | | | | | | |
| Aesthetic attribute 1 | | | | | | | | | | | | | | |
| Aesthetic attribute 2 | | | | | | | | | | | | | | |
| Aesthetic attribute (n) | | | | | | | | | | | | | | |

Figure 6

Consumer Attribute Criteria Input vs. "Listen To Your Food" Compliance and Non-compliance Response Format

TRANSFORMATION SYSTEM FOR NUTRITIONAL SUBSTANCES

RELATED PATENT APPLICATIONS

This application is a continuation-in-part of Utility application Ser. No. 13/560,965 filed Jul. 27, 2012, which is a continuation of Utility application Ser. No. 13/485,863 filed May 31, 2012, which, in turn, claims the benefit of U.S. Provisional Patent Application Ser. No. 61/625,002, filed Apr. 16, 2012; and U.S. Provisional Patent Application, 61/625, 010, filed Apr. 16, 2012, the contents of which are incorporated herein by reference in their entirety.

FIELD OF THE INVENTION

The present inventions relate to transformation of nutritional substances in conjunction with the collection, transmission, and use of information regarding source and preservation and transformation information of the nutritional substance.

BACKGROUND OF THE INVENTION

Nutritional substances are traditionally grown (plants), raised (animals) or synthesized (synthetic compounds). Additionally, nutritional substances can be found in a wild, non-cultivated form, which can be caught or collected. While the collectors and creators of nutritional substances generally obtain and/or generate information about the source, history, caloric content and/or nutritional content of their products, they generally do not pass such information along to the users of their products. One reason is the nutritional substance industries have tended to act like "silo" industries. Each group in the food and beverage industry: growers, packagers, processors, distributors, retailers, and preparers work separately, and either shares no information, or very little information, between themselves. There is generally no consumer access to, and little traceability of, information regarding the creation and/or origin, preservation, processing, preparation, or consumption of nutritional substances. It would be desirable for such information be available to the consumers of nutritional substances, as well as all participants in the food and beverage industry—the nutritional substance supply system.

While the nutritional substance supply system has endeavored over the last 50 years to increase the caloric content of nutritional substances produced (which has help reduce starvation in developing countries, but has led to obesity problems in developed countries), maintaining, or increasing, the nutritional content of nutritional substances has been a lower priority. Caloric content refers to the energy in nutritional substances, commonly measured in calories. The caloric content could be represented as sugars and/or carbohydrates in the nutritional substances. The nutritional content, also referred to herein as nutritional value, of foods and beverages, as used herein, refers to the non-caloric content of these nutritional substances which are beneficial to the organisms which consume these nutritional substances. For example, the nutritional content of a nutritional substance could include vitamins, minerals, proteins, and other non-caloric components which are necessary, or at least beneficial, to the organism consuming the nutritional substances.

While there has recently been greater attention by consumer organizations, health organizations and the public to the nutritional content of foods and beverages, the food and beverage industry has been slow in responding to this attention. One reason for this may be that since the food and beverage industry operates as silos of those who create nutritional substances, those who preserve and transport nutritional substances, those who transform nutritional substances, and those who finally prepare the nutritional substances for consumption by the consumer, there has been no system wide coordination of management of nutritional content. While each of these silo industries may be able to maintain or increase the nutritional content of the foods and beverages they handle, each silo industry has only limited information and control of the nutritional substances they receive, and the nutritional substances they pass along.

As consumers better understand their need for nutritional substances with higher nutritional content, they will start demanding that the food and beverage industry offer products which include higher nutritional content, and/or at least information regarding nutritional content of such products. In fact, consumers are already willing to pay higher prices for higher nutritional content. This can be seen at high-end grocery stores which offer organic, minimally processed, fresh, non-adulterated nutritional substances. Further, as societies and governments seek to improve their constituents' health and lower healthcare costs, incentives and/or mandates will be given to the food and beverage industry to track, maintain, and/or increase the nutritional content of nutritional substances they handle. There will be a need, not only within each food and beverage industry silo to maintain or improve the nutritional content of their products, but an industry-wide solution to allow the management of nutritional content across the entire cycle from creation to consumption. In order to manage the nutritional content of nutritional substances across the entire cycle from creation to consumption, the nutritional substance industry will need to identify, track, measure, estimate, preserve, transform, condition, and record nutritional content for nutritional substances. Of particular importance is the measurement, estimation, and tracking of changes to the nutritional content of a nutritional substance from creation to consumption. This information could be used, not only by the consumer in selecting particular nutritional substances to consume, but could be used by the other food and beverage industry silos, including creation, preservation, transformation, and conditioning, to make decisions on how to create, handle and process nutritional substances. Additionally, those who sell nutritional substances to consumers, such as restaurants and grocery stores, could communicate perceived qualitative values of the nutritional substance in their efforts to market and position their nutritional substance products. Further, a determinant of price of the nutritional substance could be particular nutritional, organoleptic, or aesthetic values, and if changes to those values are perceived as desirable. For example, if a desirable value has been maintained, improved, or minimally degraded, it could be marketed as a premium product and dynamically priced according to its current desirable value. This information could even give consumers the ability to rapidly query nutritional substances regarding compliance, or non-compliance, with the consumer's requirements for the components of the nutritional substance, the integrity of the nutritional substance, the nutritional, organoleptic, and aesthetic values of the nutritional substance, and changes to the nutritional, organoleptic, and aesthetic values of the nutritional substance. In other words, this information could give food a voice, and enable consumers to listen to food.

For example, the grower of sweet corn generally only provides basic information as the variety and grade of its corn to the packager, who preserves and ships the corn to a producer for use in a ready-to-eat dinner. The packager may only tell the producer that the corn has been frozen as loose kernels of sweet corn. The producer may only provide the consumer with rudimentary instructions how to cook or reheat the ready-to-eat dinner in a microwave oven, toaster oven or conventional oven, and only tell the consumer that the dinner contains whole kernel corn among the various items in the dinner. Finally, the consumer of the dinner will likely keep her opinions on the quality of the dinner to herself, unless it was an especially bad experience, where she might contact the producer's customer support program to complain. Very minimal, or no, information on the nutritional content of the ready-to-eat dinner is passed along to the consumer. The consumer knows essentially nothing about changes (generally a degradation, but could be a maintenance or even an improvement) to the nutritional content of the sweet corn from creation, processing, packaging, cooking, preservation, preparation by consumer, and finally consumption by the consumer.

Consumers' needs are changing as consumers are demanding healthier foods, such as "organic foods." Customers are also asking for more information about the content, origin, and creation of nutritional substances they consume, such as specific characteristics' relating not only to nutritional content, but to allergens or digestive intolerances, if it is organic, was it wild caught, was is wild harvest. Consumers are also asking for more information regarding the integrity of the nutritional substances they consume, such as if there are additives, preservatives, or substitutes, are there contaminants such as pesticides, hormones, antibiotics, heavy metals, bacteria, has the nutritional substance been tampered with, has it spoiled, has it been stored appropriately, and so on. For example, nutritional substances which contain lactose, gluten, nuts, dyes, etc. need to be avoided by certain consumers. However, the producer of the ready-to-eat dinner, in the prior example, has very little information to share other than possibly the source of the elements of the ready-to-eat dinner and its processing steps in preparing the dinner. Generally, the producer of the ready-to-eat dinner does not know the nutritional content and organoleptic state and aesthetic condition of the product after it has been reheated or cooked by the consumer, cannot predict changes to these properties, and cannot inform a consumer of this information to enable the consumer to better meet their needs. For example, the consumer may want to know what proportion of desired organoleptic properties or values, desired nutritional content or values, or desired aesthetic properties or values of the corn in the ready-to-eat dinner remain after cooking or reheating, and the change in the desired nutritional content or values, the desired organoleptic properties or values, or the desired aesthetic properties or values (usually a degradation, but could be a maintenance or even improvement). There is a need to preserve, measure, estimate, store and/or transmit information regarding such nutritional, organoleptic, and aesthetic values, including changes to these values, throughout the nutritional substance supply system. There is also a need to preserve, measure, estimate, store and/or transmit information regarding the nutritional substance content and integrity.

The caloric and nutritional content information for a prepared food that is provided to the consumer is often minimal. For example, when sugar is listed in the ingredient list, the consumer generally does receive any information about the source of the sugar, which can come from a variety of plants, such as sugarcane, beets, or corn, which will affect its nutritional content. Conversely, some nutritional information that is provided to consumers is so detailed and static, the consumer can do little with it. For example, this list of ingredients is from a nutritional label on a consumer product: Vitamins—A 355 IU 7%, E 0.8 mg 4%, K 0.5 mcg, 1%, Thiamin 0.6 mg 43%, Riboflavin 0.3 mg 20%, Niacin 6.0 mg 30%, B6 1.0 mg 52%, Foliate 31.5 mcg 8%, Pantothenic 7%; Minerals Calcium 11.6 1%, Iron 4.5 mg 25%, Phosphorus 349 mg 35%, Potassium 476 mg 14%, Sodium 58.1 mg 2%, Zinc 3.7 mg 24%, Copper 0.5 mg 26%, Manganese 0.8 mg 40%, Selenium 25.7 mcg 37%; Carbohydrate 123 g, Dietary fiber 12.1 g, Saturated fat 7.9 g, Monosaturated Fat 2.1 g, Polysaturated Fat 3.6 g, Omega 3 fatty acids 108 g, Omega 6 fatty acids 3481, Ash 2.0 g and Water 17.2 g. (%=Daily Value). There is a need to provide information about nutritional substances in a dynamic and meaningful manner. Such information needs to be presented in a manner that meets the specific needs of a particular consumer. For example, consumers with a medical condition, such as diabetes, would want to track specific information regarding nutritional values associated with sugar and other nutrients in the foods and beverages they consume, and would benefit further from knowing changes in these values or having tools to quickly indicate or estimate these changes in a retrospective, current, or prospective fashion.

In fact, each silo in the food and beverage industry already creates and tracks some information, including caloric and nutritional information, about their product internally. For example, the farmer who grew the corn knows the variety of the seed, condition of the soil, the source of the water, the fertilizers and pesticides used, and can measure the caloric and nutritional content at creation. The packager of the corn knows when it was picked, how it was transported to the packaging plant, how the corn was preserved and packaged before being sent to the ready-to-eat dinner producer, when it was delivered to the producer, and what degradation to caloric and nutritional content has occurred. The producer knows the source of each element of the ready-to-eat dinner, how it was processed, including the recipe followed, and how it was preserved and packaged for the consumer. Not only does such a producer know what degradation to caloric and nutritional content occurred, the producer can modify its processing and post-processing preservation to minimally affect nutritional content. The preparation of the nutritional substance for consumption can also degrade the nutritional content of nutritional substances. Finally, the consumer knows how she prepared the dinner, what condiments were added, and whether she did or did not enjoy it.

If there was a mechanism to share this information, the quality of the nutritional substances, including caloric and nutritional, organoleptic, and aesthetic value, could be preserved and improved. Consumers could be better informed about nutritional substances they select and consume, including the state, and changes in the state, of the nutritional substance throughout its lifecycle from creation to consumption. The efficiency and cost effectiveness of nutritional substances could also be improved. Feedback within the entire chain from creator to consumer could provide a closed-loop system that could improve quality (taste, appearance, and caloric and nutritional content), efficiency, value and profit. For example, in the milk supply chain, at least 10% of the milk produced is wasted due to safety margins included in product expiration dates. The use of more accurate tracking information, measured quality (including nutritional content) information, and historical environmental information could substantially reduce such waste. Collecting, preserving, measuring and/or tracking information about a nutritional substance in the nutritional substance supply system, would allow needed accountability. This information could even give consumers the ability to rapidly query nutritional substances regarding compliance, or non-compliance, with the consumer's requirements for the components of the nutritional substance, the integrity of the nutritional substance, the nutritional, organoleptic, and aesthetic values of the nutritional substance, and changes to the nutritional, organoleptic, and aesthetic values of the nutritional substance. This information could also be utilized to dynamically establish a price for the nutritional substance. In other words, this information could give food a voice, and enable consumers to listen to food. There would be nothing to hide.

As consumers are demanding more information about what they consume, they are asking for products that have higher nutritional content and more closely match good nutritional requirements, and would like nutritional products to actually meet their specific nutritional requirements. While grocery stores, restaurants, and all those who process and sell food and beverages may obtain some information from current nutritional substance tracking systems, such as labels, these current systems can provide only limited information.

Traditional food processors take nutritional substances from producers and transform them into nutritional substances for consumption by consumers. While they have some knowledge of the nutritional substances they purchase, and make such selections to meet the needs of the consumers, they generally do not transmit that information along to consumers, nor change the way they transform the nutritional substances based on the history or current condition of the nutritional substances they receive for transformation.

An important issue in the creation, preservation, transformation, conditioning, and consumption of nutritional substances are the changes that occur in nutritional substances due to a variety of internal and external factors. Because nutritional substances are composed of biological, organic, and/or chemical compounds, they are generally subject to degradation. This degradation generally reduces the nutritional, organoleptic, and/or aesthetic values of nutritional substances. While not always true, nutritional substances are best consumed at their point of creation. However, being able to consume nutritional substances at the farm, at the slaughterhouse, at the fishery, or at the food processing plant is at least inconvenient, if not impossible. Currently, the food and beverage industry attempts to minimize the loss of nutritional value (often through the use of additives or preservatives), and/or attempts to hide this loss of nutritional value from consumers.

Overall, the examples herein of some prior or related systems and their associated limitations are intended to be illustrative and not exclusive. Other limitations of existing or prior systems will become apparent to those of skill in the art upon reading the following Detailed Description.

OBJECTS OF THE INVENTION

It is an object of present invention that a transformer of nutritional substance maintains creation and/or preservation information for components of a transformed nutritional substance.

It is another object of the present invention that a transformer of nutritional substance maintains creation and/or preservation information for components of a transformed nutritional substance and additionally provides information regarding the transformation.

It is an object of the present invention that a transformer of nutritional substance maintains creation and/or packaging information for components of a transformed nutritional substance.

It is another object of the present invention that a transformer of nutritional substance maintains creation and/or packaging information for components of a transformed nutritional substance and additionally provides information regarding the transformation.

It is a further object of the present invention to utilize the source and packaging and preservation information to modify or adapt the transformation of the nutritional substance to preserve and/or minimize degradation of and/or improve nutritional value and/or quality of the transformed nutritional substance. Additionally, such information can be used by an automated system to adaptively transform the nutritional substance so as to preserve and/or minimize degradation of and/or improve nutritional, organoleptic, or aesthetic value and/or quality of the transformed nutritional substance.

It is an object of the present invention to minimize and/or track degradation of nutritional, organoleptic, and/or aesthetic value of nutritional substances, and/or collect, store, and/or transmit information regarding this degradation.

SUMMARY OF THE INVENTION

In an embodiment of the present invention, the transformer of nutritional substances obtains and transmits source and/or preservation information to be utilized by users and/or consumers of the transformed nutritional substance.

In another embodiment of the present invention, the transformer of nutritional substances obtains and transmits source and/or preservation information and information regarding the transformation to be utilized by users and/or consumers of the transformed nutritional substance.

In an embodiment of the present invention, the transformer of nutritional substances obtains and transmits source and/or packaging information to be utilized by users and/or consumers of the transformed nutritional substance.

In another embodiment of the present invention, the transformer of nutritional substances obtains and transmits source and/or packaging information and information regarding the transformation to be utilized by users and/or consumers of the transformed nutritional substance.

In a further embodiment of the present invention, source and/or packaging and/or preservation information is used by the transformer to modify or adapt the process for transformation of the nutritional substance so as to preserve and/or minimize degradation of and/or improve nutritional, organoleptic, or aesthetic value and/or quality of the transformed nutritional substance.

In another embodiment of the present invention, source and/or packaging and/or preservation information for multiple components of the nutritional substance being transformed are used to adaptively transform the nutritional substance so as to preserve and/or minimize degradation of and/or improve nutritional, organoleptic, or aesthetic value and/or quality of the transformed nutritional substance or of specific components of the transformed nutritional substance.

In another embodiment of the present invention information regarding a change of nutritional, organoleptic, and/or aesthetic value of nutritional substances, collectively and individually referred to herein as $\Delta N$, is: measured or collected or calculated or created or estimated or indicated or determined in any suitable manner; stored and/or tracked and/or transmitted and/or processed prior to transformation and/or following transformation, such that the degradation of specific nutritional, organoleptic, and/or aesthetic values can be minimized and specific residual nutritional, organoleptic, and/or aesthetic value can be optimized. A change of nutritional, organoleptic, and/or aesthetic value may not occur, in which case $\Delta N$ would be zero. The change of nutritional, organoleptic, and/or aesthetic value may be a degradation, in which case ΔN would be negative. The change of nutritional, organoleptic, and/or aesthetic value may be an improvement, in which case ΔN would be positive.

An embodiment of the present invention provides a system for the creation, collection, storage, transmission, and/or processing of information regarding nutritional substances so as to improve, maintain, or minimize degradation of nutritional, organoleptic, and/or aesthetic value of nutritional substances. Additionally, the present invention provides such information for use by the creators, preservers, transformers, conditioners, and consumers of nutritional substances. The nutritional information creation, preservation, and transmission system of the present invention should allow the nutritional substance supply system to improve its ability to minimize degradation of nutritional, organoleptic and/or aesthetic value of the nutritional substance, and/or inform the consumer about such degradation. The ultimate goal of the nutritional substance supply system is to minimize degradation of nutritional, organoleptic and/or aesthetic values, or as it relates to ΔN, minimize the negative magnitude of ΔN. However, an interim goal should be providing consumers with significant information regarding any change, particularly degradation, of nutritional, organoleptic and/or aesthetic values of nutritional substances consumers select and consume, the ΔN, such that desired information regarding specific residual nutritional, organoleptic, and/or aesthetic values can be ascertained using the ΔN. Entities within the nutritional substance supply system who provide such ΔN information regarding nutritional substances, particularly regarding degradation, will be able to differentiate their products from those who obscure and/or hide such information. Additionally, such entities should be able to charge a premium for products which either maintain their nutritional, organoleptic, and/or aesthetic value, or supply more complete information about changes in their nutritional, organoleptic, and/or aesthetic value, the ΔN.

Other advantages and features will become apparent from the following description and claims. It should be understood that the description and specific examples are intended for purposes of illustration only and not intended to limit the scope of the present disclosure.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 6 shows in tabular form consumer attribute criteria input for nutritional substances vs. compliance and non-compliance responses from a system according to the present invention.

Figure 1:
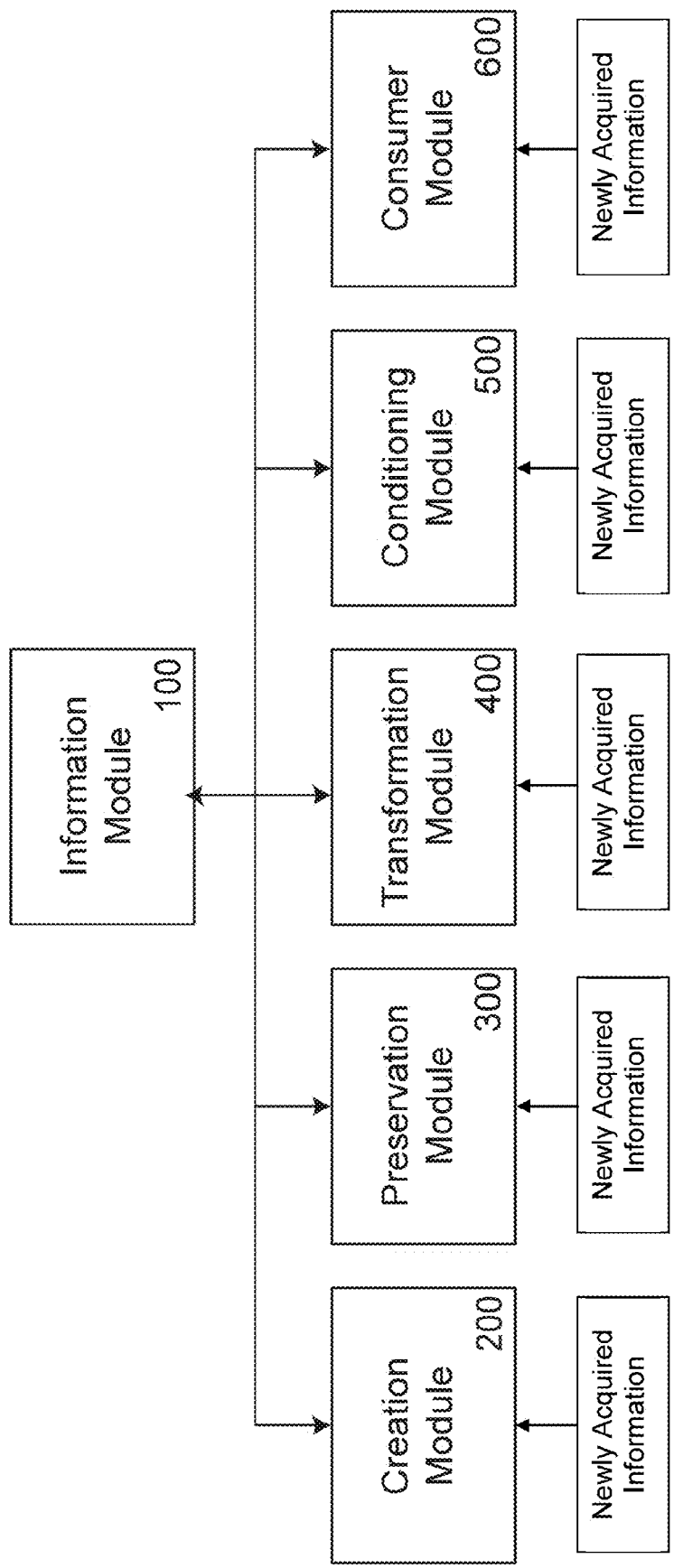
FIG. 1 shows a schematic functional block diagram of a nutritional substance supply relating to the present invention.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION OF THE INVENTION

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

The following discussion provides a brief, general description of a representative environment in which the invention can be implemented. Although not required, aspects of the invention may be described below in the general context of computer-executable instructions, such as routines executed by a general-purpose data processing device (e.g., a server computer or a personal computer). Those skilled in the relevant art will appreciate that the invention can be practiced with other communications, data processing, or computer system configurations, including: wireless devices, Internet appliances, hand-held devices (including personal digital assistants (PDAs)), wearable computers, all manner of cellular or mobile phones, multi-processor systems, microprocessor-based or programmable consumer electronics, set-top boxes, network PCs, mini-computers, mainframe computers, and the like. Indeed, the terms "controller," "computer," "server," and the like are used interchangeably herein, and may refer to any of the above devices and systems.

While aspects of the invention, such as certain functions, are described as being performed exclusively on a single device, the invention can also be practiced in distributed environments where functions or modules are shared among disparate processing devices. The disparate processing devices are linked through a communications network, such as a Local Area Network (LAN), Wide Area Network (WAN), or the Internet. In a distributed computing environment, program modules may be located in both local and remote memory storage devices.

Aspects of the invention may be stored or distributed on tangible computer-readable media, including magnetically or optically readable computer discs, hard-wired or preprogrammed chips (e.g., EEPROM semiconductor chips), nanotechnology memory, biological memory, or other data storage media. Alternatively, computer implemented instructions, data structures, screen displays, and other data related to the invention may be distributed over the Internet or over other networks (including wireless networks), on a propagated signal on a propagation medium (e.g., an electromagnetic wave(s), a sound wave, etc.) over a period of time. In some implementations, the data may be provided on any analog or digital network (packet switched, circuit switched, or other scheme).

In some instances, the interconnection between modules is the internet, allowing the modules (with, for example, WiFi capability) to access web content offered through various web servers. The network may be any type of cellular, IP-based or converged telecommunications network, including but not limited to Global System for Mobile Communications (GSM), Time Division Multiple Access (TDMA), Code Division Multiple Access (CDMA), Orthogonal Frequency Division Multiple Access (OFDM), General Packet Radio Service (GPRS), Enhanced Data GSM Environment (EDGE), Advanced Mobile Phone System (AMPS), Worldwide Interoperability for Microwave Access (WiMAX), Universal Mobile Telecommunications System (UMTS), Evolution-Data Optimized (EVDO), Long Term Evolution (LTE), Ultra Mobile Broadband (UMB), Voice over Internet Protocol (VoIP), Unlicensed Mobile Access (UMA), etc.

The modules in the systems can be understood to be integrated in some instances and in particular embodiments, only particular modules may be interconnected.

FIG. 1 shows the components of a nutritional substance industry 10. It should be understood that this could be the food and beverage ecosystem for human consumption, but could also be the feed industry for animal consumption, such as the pet food industry. A goal of the present invention for nutritional substance industry 10 is to create, preserve, transform and trace the change in nutritional, organoleptic and/or aesthetic values of nutritional substances, collectively and individually also referred to herein as $\Delta N$, through their creation, preservation, transformation, conditioning and consumption. While the nutritional substance industry 10 can be composed of many companies or businesses, it can also be integrated into combinations of business serving many roles, or can be one business or even individual. Since $\Delta N$ is a measure of the change in a value of a nutritional substance, knowledge of a prior value (or state) of a nutritional substance and the $\Delta N$ value will provide knowledge of the changed value (or state) of a nutritional substance, and can further provide the ability to estimate a change in value (or state).

Module 200 is the creation module. This can be a system, organization, or individual which creates and/or originates nutritional substances. Examples of this module include a farm which grows produce; a ranch which raises beef; an aquaculture farm for growing shrimp; a factory that synthesizes nutritional compounds; a collector of wild truffles; or a deep sea crab trawler.

Preservation module 300 is a preservation system for preserving and protecting the nutritional substances created by creation module 200. Once the nutritional substance has been created, generally, it will need to be packaged in some manner for its transition to other modules in the nutritional substances industry 10. While preservation module 300 is shown in a particular position in the nutritional substance industry 10, following the creation module 200, it should be understood that the preservation module 300 actually can be placed anywhere nutritional substances need to be preserved during their transition from creation to consumption.

Transformation module 400 is a nutritional substance processing system, such as a manufacturer who processes raw materials such as grains into breakfast cereals. Transformation module 400 could also be a ready-to-eat dinner manufacturer who receives the components for a ready-to-eat dinner from preservation module 300 and prepares them into a frozen dinner. While transformation module 400 is depicted as one module, it will be understood that nutritional substances may be transformed by a number of transformation modules 400 on their path to consumption.

Conditioning module 500 is a consumer preparation system for preparing the nutritional substance immediately before consumption by the consumer. Conditioning module 500 can be a microwave oven, a blender, a toaster, a convection oven, a cook, etc. It can also be systems used by commercial establishments to prepare nutritional substance for consumers such as a restaurant, an espresso maker, pizza oven, and other devices located at businesses which provide nutritional substances to consumers. Such nutritional substances could be for consumption at the business or for the consumer to take out from the business. Conditioning module 500 can also be a combination of any of these devices used to prepare nutritional substances for consumption by consumers.

Consumer module 600 collects information from the living entity which consumes the nutritional substance which has passed through the various modules from creation to consumption. The consumer can be a human being, but could also be an animal, such as pets, zoo animals and livestock, which are they themselves nutritional substances for other consumption chains. Consumers could also be plant life which consumes nutritional substances to grow.

Information module 100 receives and transmits information regarding a nutritional substance between each of the modules in the nutritional substance industry 10 including, the creation module 200, the preservation module 300, the transformation module 400, the conditioning module 500, and the consumer module 600. The nutritional substance information module 100 can be an interconnecting information transmission system which allows the transmission of information between various modules. Information module 100 contains a database, also referred to herein as a dynamic nutritional value database, where the information regarding the nutritional substance resides. Information module 100 can be connected to the other modules by a variety of communication systems, such as paper, computer networks, the internet and telecommunication systems, such as wireless telecommunication systems.

Figure 2:
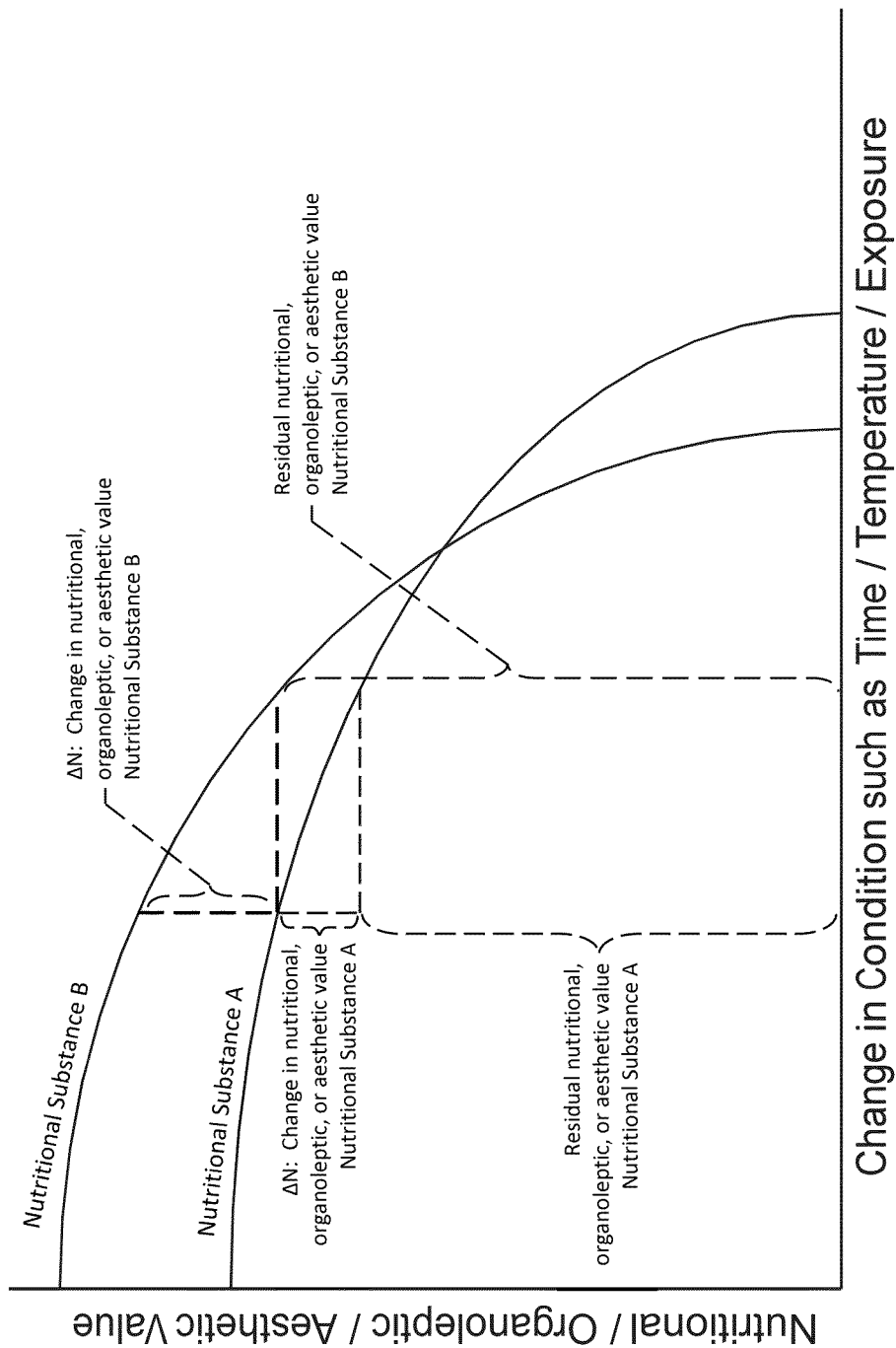
FIG. 2 shows a graph representing a value of a nutritional substance which changes according to a change of condition for the nutritional substance.

FIG. 2 is a graph showing the function of how a nutritional, organoleptic, or aesthetic value of a nutritional substance varies over the change in a condition of the nutritional substance. Plotted on the vertical axis of this graph can be either the nutritional value, organoleptic value, or even the aesthetic value of a nutritional substance. Plotted on the horizontal axis can be the change in condition of the nutritional substance over a variable such as time, temperature, location, and/or exposure to environmental conditions. This exposure to environmental conditions can include: exposure to air, including the air pressure and partial pressures of oxygen, carbon dioxide, water, or ozone; airborne chemicals, pollutants, allergens, dust, smoke, carcinogens, radioactive isotopes, or combustion byproducts; exposure to moisture; exposure to energy such as mechanical impact, mechanical vibration, irradiation, heat, or sunlight; or exposure to materials such as packaging. The function plotted as nutritional substance A could show a $\Delta N$ for milk, such as the degradation of a nutritional value of milk over time. Any point on this curve can be compared to another point to measure and/or describe the change in nutritional value, or the $\Delta N$ of nutritional substance A. The plot of the degradation in the same nutritional value of nutritional substance B, also milk, describes the change in nutritional value, or the $\Delta N$ of nutritional substance B, a nutritional substance which starts out with a higher nutritional value than nutritional substance A, but degrades over time more quickly than nutritional substance A.

If, in this example, where nutritional substance A and nutritional substance B are milk, this ΔN information regarding the nutritional substance degradation profile of each milk could be used by the consumer in the selection and/or consumption of the milk. If the consumer has this information at time zero when selecting a milk product for purchase, the consumer could consider when he plans to consume the milk, whether that is on one occasion or multiple occasions. For example, if the consumer planned to consume the milk prior to the point when the curve represented by nutritional substance B crosses the curve represented by nutritional substance A, then the consumer should choose the milk represented by nutritional substance B because it has a higher residual nutritional value until it crosses the curve represented by nutritional substance A. However, if the consumer expects to consume at least some of the milk at a point in time after the time when the curve represented by nutritional substance B crosses the curve represented by nutritional substance A, then the consumer might choose to select the milk represented by the nutritional substance A, even though milk represented by nutritional substance A has a lower nutritional value than the milk represented by nutritional substance B at an earlier time. This change to a desired nutritional value in a nutritional substance over a change in a condition of the nutritional substance described in FIG. 2 can be measured and/or controlled throughout nutritional substance supply system 10 in FIG. 1. This example demonstrates how dynamically generated information regarding a ΔN of a nutritional substance, in this case a change in nutritional value of milk, can be used to understand a rate at which that nutritional value changes or degrades; when that nutritional value expires; and a residual nutritional value of the nutritional substance over a change in a condition of the nutritional substance, in this example a change in time. This ΔN information could further be used to determine a best consumption date for nutritional substance A and B, which could be different from each other depending upon the dynamically generated information generated for each. This ΔN information could also be used to determine dynamic pricing for nutritional substance A and B, wherein the dynamic pricing is dependent on a residual nutritional, organoleptic, and/or aesthetic value of the corresponding nutritional substance.

In FIG. 1, Creation module 200 can dynamically encode nutritional substances to enable the tracking of changes in nutritional, organoleptic, and/or aesthetic value of the nutritional substance, or ΔN. This dynamic encoding, also referred to herein as a dynamic information identifier, can replace and/or complement existing nutritional substance marking systems such as barcodes, labels, and/or ink markings. This dynamic encoding, or dynamic information identifier, can be used to make nutritional substance information from creation module 200 available to information module 100 for use by preservation module 300, transformation module 400, conditioning module 500, and/or consumption module 600, which includes the ultimate consumer of the nutritional substance. The information may relate to the nutritional, organoleptic, and aesthetic value of the nutritional substance, such as changes in the nutritional, organoleptic, and aesthetic value of the nutritional substance (ΔN), the residual nutritional, organoleptic, and aesthetic value of the nutritional substance. The information may further include information derived or responsive to these dynamic nutritional, organoleptic, and aesthetic values of the nutritional substance, such as dynamic pricing information. The information may further relate to origin and creation and composition of the components of the nutritional substance and the integrity of the nutritional substance, such as information regarding additives, preservatives, or substitutes, information regarding contaminants such as pesticides, hormones, antibiotics, heavy metals, or bacteria, and information related to or indicating product tampering, spoiled, inappropriate storage conditions, appropriately, and any other form of product adulteration. One method of marking the nutritional substance with a dynamic information identifier by creation module 200, or any other module in nutritional supply system 10, could include an electronic tagging system, such as the tagging system manufactured by Kovio of San Jose, Calif., USA. Such thin film chips can be used not only for tracking nutritional substances, by can include components to measure attributes of nutritional substances, and record and transmit such information. Such information may be readable by a reader including a satellite-based system. Such a satellite-based nutritional substance information tracking system could comprise a network of satellites with coverage of some or all the surface of the earth, so as to allow information module 100 real time, or near real time updates about a ΔN of a particular nutritional substance.

Preservation module 300 includes packers and shippers of nutritional substances. The tracking of changes in nutritional, organoleptic, and/or aesthetic values, or a ΔN, during the preservation period within preservation module 300 allows for dynamic expiration dates for nutritional substances. For example, expiration dates for dairy products are currently based generally only on time using assumptions regarding minimal conditions at which dairy products are maintained. This extrapolated expiration date is based on a worst-case scenario for when the product becomes unsafe to consume during the preservation period. In reality, the degradation of dairy products may be significantly less than this worst-case. If preservation module 300 could measure or derive the actual degradation information such as ΔN, an actual expiration date, referred to herein as a dynamic expiration date, can be determined dynamically, and could be significantly later in time than an extrapolated expiration date. This would allow the nutritional substance supply system to dispose of fewer products due to expiration dates. This ability to dynamically generate expiration dates for nutritional substances is of particular significance when nutritional substances contain few or no preservatives. Such products are highly valued throughout nutritional substance supply system 10, including consumers who are willing to pay a premium for nutritional substances with few or no preservatives.

It should be noted that a dynamic expiration date need not be indicated numerically (i.e., as a numerical date) but could be indicated symbolically as by the use of colors—such as green, yellow and red employed on semaphores—or other designations. In those instances, the dynamic expiration date would not be interpreted literally but, rather, as a dynamically-determined advisory date. In practice a dynamic expiration date will be provided for at least one component of a single or multi-component nutritional substance. For multi-component nutritional substances, the dynamic expiration date could be interpreted as a "best' date for consumption for particular components.

By law, in many localities, food processors such as those in transformation module 400 are required to provide nutritional substance information regarding their products. Often, this information takes the form of a nutritional table applied to the packaging of the nutritional substance. Currently, the information in this nutritional table is based on averages or minimums for their typical product. Using the nutritional substance information from information module 100 provided by creation module 200, preservation module 300, and/or information from the transformation of the nutritional substance by transformation module 400, the food processor could include a dynamically generated nutritional value table, also referred to herein as a dynamic nutritional value table, for the actual nutritional substance being supplied. The information in such a dynamic nutritional value table could be used by conditioning module 500 in the preparation of the nutritional substance, and/or used by consumption module 600, so as to allow the ultimate consumer the ability to select the most desirable nutritional substance which meets their needs, and/or to track information regarding nutritional substances consumed.

The change in nutritional, organoleptic, and/or aesthetic value, or $\Delta N$, by conditioning module 500 is currently not tracked or provided to the consumer. However, using information provided by information module 100 from creation module 200, preservation module 300, transformation module 400, and/or information measured or generated by conditioning module 500, conditioning module 500 could provide the consumer with the actual, and/or estimated change in nutritional, organoleptic, and/or aesthetic values of the nutritional substance, or $\Delta N$. Such information regarding the change to nutritional, organoleptic and/or aesthetic value of the nutritional substance, or $\Delta N$, could be provided not only to the consumer, but could also be provided to information module 100 for use by creation module 200, preservation module 300, transformation module 400, so as to track, and possibly improve nutritional substances throughout the entire nutritional substance supply system 10.

The information regarding nutritional substances provided by information module 100 to consumption module 600 can replace or complement existing information sources such as recipe books, food databases like www.epicurious.com, and Epicurious apps. Through the use of specific information regarding a nutritional substance from information module 100, consumers can use consumption module 600 to select nutritional substances according to nutritional, organoleptic, and/or aesthetic values. This will allow consumers to make informed decisions regarding nutritional substance additives, preservatives, genetic modifications, origins, traceability, and other nutritional substance attributes. This information can be provided by consumption module 600 through personal computers, laptop computers, tablet computers, and/or smartphones. Software running on these devices can include dedicated computer programs, modules within general programs, and/or smartphone apps. An example of such a smartphone app regarding nutritional substances is the iOS ShopNoGMO from the Institute for Responsible Technology. This iPhone app allows consumers access to information regarding non-genetically modified organisms they may select. Additionally, consumption module 600 may provide information for the consumer to operate conditioning module 500 in such a manner as to preserve or optimize or minimize degradation of nutritional, organoleptic, and/or aesthetic value.

Through the use of nutritional substance information available from information module 100 nutritional substance supply system 10 can track nutritional, organoleptic, and/or aesthetic value. Using this information, nutritional substances travelling through nutritional substance supply system 10 can be dynamically valued and priced according to nutritional, organoleptic, and/or aesthetic values. For example, nutritional substances with longer dynamic expiration dates (longer shelf life) may be more highly valued than nutritional substances with shorter expiration dates. Additionally, nutritional substances with higher nutritional, organoleptic, and/or aesthetic values may be more highly valued, not just by the consumer, but also by each entity within nutritional substance supply system 10. This is because each entity will want to start with a nutritional substance with higher nutritional, organoleptic, and/or aesthetic value before it performs its function and passes the nutritional substance along to the next entity.

During the period of implementation of the present inventions, there will be nutritional substances being marketed including information-enabled nutritional substances, that is to say nutritional substances provided with dynamic information identifiers according to the present invention, and nutritional substances which are not information enabled, or dumb nutritional substances. Information-enabled nutritional substances would be available in virtual internet marketplaces, as well as traditional marketplaces. Because of information provided by information-enabled nutritional substances, entities within the nutritional substance supply system 10, including consumers, would be able to review and select information-enabled nutritional substances for purchase. It should be expected that, initially, the information-enabled nutritional substances would enjoy a higher market value and price than dumb nutritional substances. However, as information-enabled nutritional substances become more the norm, the cost savings from less waste due to degradation of information-enabled nutritional substances could lead to their price actually becoming less than dumb nutritional substances.

For example, the producer of a ready-to-eat dinner would prefer to use corn of a high nutritional, organoleptic, and/or aesthetic value in the production of its product, the ready-to-eat dinner, so as to produce a premium product of high nutritional, organoleptic, and/or aesthetic value. Depending upon the levels of the nutritional, organoleptic, and/or aesthetic values, the ready-to-eat dinner producer may be able to charge a premium price and/or differentiate its product from that of other producers. When selecting the corn to be used in the ready-to-eat dinner, the producer will seek corn of high nutritional, organoleptic, and/or aesthetic value from preservation module 300 that meets its requirements for nutritional, organoleptic, and/or aesthetic value. The packager/shipper of preservation module 300 would also be able to charge a premium for corn which has high nutritional, organoleptic, and/or aesthetic values. And finally, the packager/shipper of preservation module 300 will select corn of high nutritional, organoleptic, and/or aesthetic value from the grower of creation module 200, who will also be able to charge a premium for corn of high nutritional, organoleptic, and/or aesthetic values.

The change to nutritional, organoleptic, and/or aesthetic value for a nutritional substance, or $\Delta N$, tracked through nutritional substance supply system 10 through nutritional substance information from information module 100 can be preferably determined from measured information. However, some or all such nutritional substance $\Delta N$ information may be derived through measurements of environmental conditions of the nutritional substance as it travelled through nutritional substance supply system 10. Additionally, some or all of the nutritional substance $\Delta N$ information can be derived from $\Delta N$ data of other nutritional substances which have travelled through nutritional substance supply system 10. Finally, nutritional substance $\Delta N$ information can also be derived from laboratory experiments performed on other nutritional substances, which may approximate conditions and/or processes to which the actual nutritional substance has been exposed.

For example, laboratory experiments can be performed on bananas to determine effect on or change in nutritional, organoleptic, and/or aesthetic value, or $\Delta N$, for a variety of environmental conditions bananas may be exposed to during packaging and shipment in preservation module 300. Using this experimental data, tables and/or algorithms could be developed which would predict the level of change of nutritional, organoleptic, and/or aesthetic values, or ΔN, for a particular banana based upon information collected regarding the environmental conditions to which the banana was exposed during its time in preservation module 300. While the ultimate goal for nutritional substance supply system 10 would be the actual measurement of nutritional, organoleptic, and/or aesthetic values to determine ΔN, use of derived nutritional, organoleptic, and/or aesthetic values from experimental data to determine ΔN would allow more accurate tracking of changes to nutritional, organoleptic, and/or aesthetic values while technology and systems are put in place to allow actual measurement.

Figure 3:
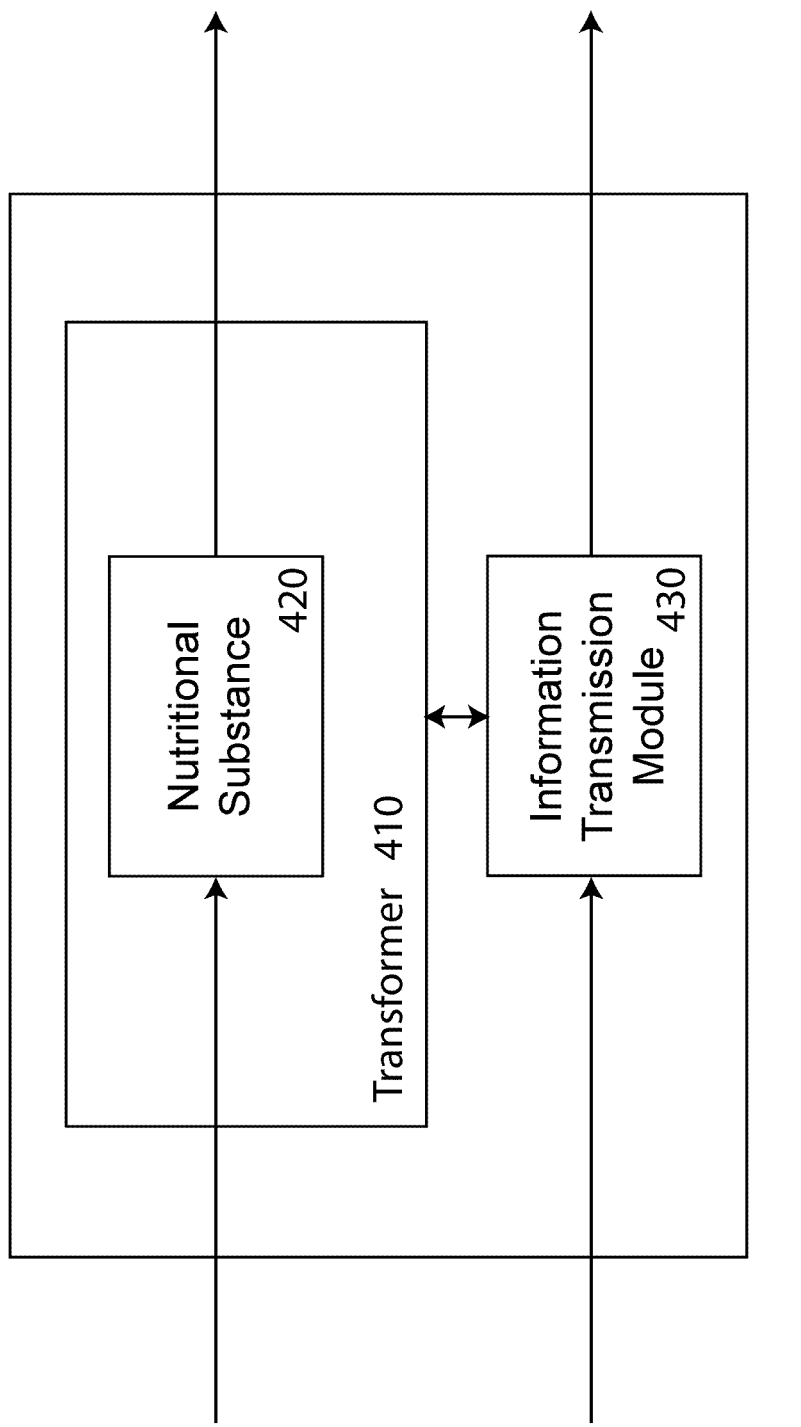
FIG. 3 shows a schematic functional block diagram of the transformation module 400 according to the present invention.

FIG. 3 shows an embodiment of transformation module 400 of the present invention. Transformation module 400 includes transformer 410, which acts upon nutritional substance 420, and information transmission module 430. When transformer 410 receives a nutritional substance 420, information transmission module 430 also receives, or retrieves information about the particular nutritional substance 420 that is to be transformed. This information can include creation information, preservation information, packaging information, shipping information, and possibly previous transformation information. After nutritional substance 420 has been transformed by transformer 410, such information is passed along with the transformed nutritional substance 420 by the information transmission module 430.

For example, sweet corn that arrives for processing by transformer 410 has information associated with it, including the corn variety, where it was planted, when it was planted, when it was picked, the soil it was grown in, the water used for irrigation, and the fertilizers and pesticides that were used during its growth. There may also be information on nutritional and/or organoleptic and/or aesthetic values of the corn when it was preserved for shipment. This information may be stored in the labeling of the corn. However, it may be stored in a database maintained by the grower, shipper, or the nutritional substances industry, also referred to herein as a dynamic nutritional value database. Such information could be accessed by means of telecommunications systems, such as wireless telecommunication systems.

Additionally, the corn may have information associated with it regarding how it was preserved for shipment from the farm to transformation module 400. Such information may include historical information on the environment exterior the container it was shipped in, internal conditions of the container and actual information about the corn during the shipment. Additionally, if the preservation system acted upon such information in preserving the corn, information about the preservation measures may also be available. Such information may be stored in the preservation system. However, it may be stored in a database maintained by the grower, shipper, or the nutritional substances industry, also referred to herein as a dynamic nutritional value database. Such information could be accessed by means of telecommunications systems, such as wireless telecommunication systems.

In the example where the nutritional substance 420 is corn, transformer 410 removes the husk and the silk from the corn. It then separates the kernels from the cob, washes the kernels, and cooks them. Finally, transformer 410 packages the cooked corn in a can and labels the can. The label on the can may contain all the information provided to information transmission module 430. Preferably, this information is referenced by a dynamic encode or tag, herein referred to as a dynamic information identifier, which identifies the information regarding the corn in the can that is being transmitted by information transmission module 430.

In practice, information transmission module 430 would receive the information regarding the nutritional substance 420 from a database that is being used to track the corn during its journey from the farm to the consumer. When transformer 410 transforms nutritional substance 420, information transmission module 430 retrieves the appropriate information from the database and transmits it to another database. Alternatively, the information retrieved by transmission module 430 would be transmitted back to the original database, noting that the transformation had occurred. Preferably, the information regarding the corn retrieved by transmission module 430 would simply be appended with the information that the transformation had occurred. Such databases are individually and collectively referred to herein as a dynamic nutritional value database.

If the nutritional substance 420 can no longer be tracked by the reference information or dynamic information identifier that accompanied the nutritional substance from the creator, then new reference information or a new dynamic information identifier may be created. For example, if the corn is combined with lima beans in the transformer 410, to make succotash, then the information for each may be combined and assigned a new reference number or a new dynamic information identifier. Preferably, a new entry is created in the dynamic nutritional value database, with references to the information related to the corn and the information related to the lima beans.

Figure 4:
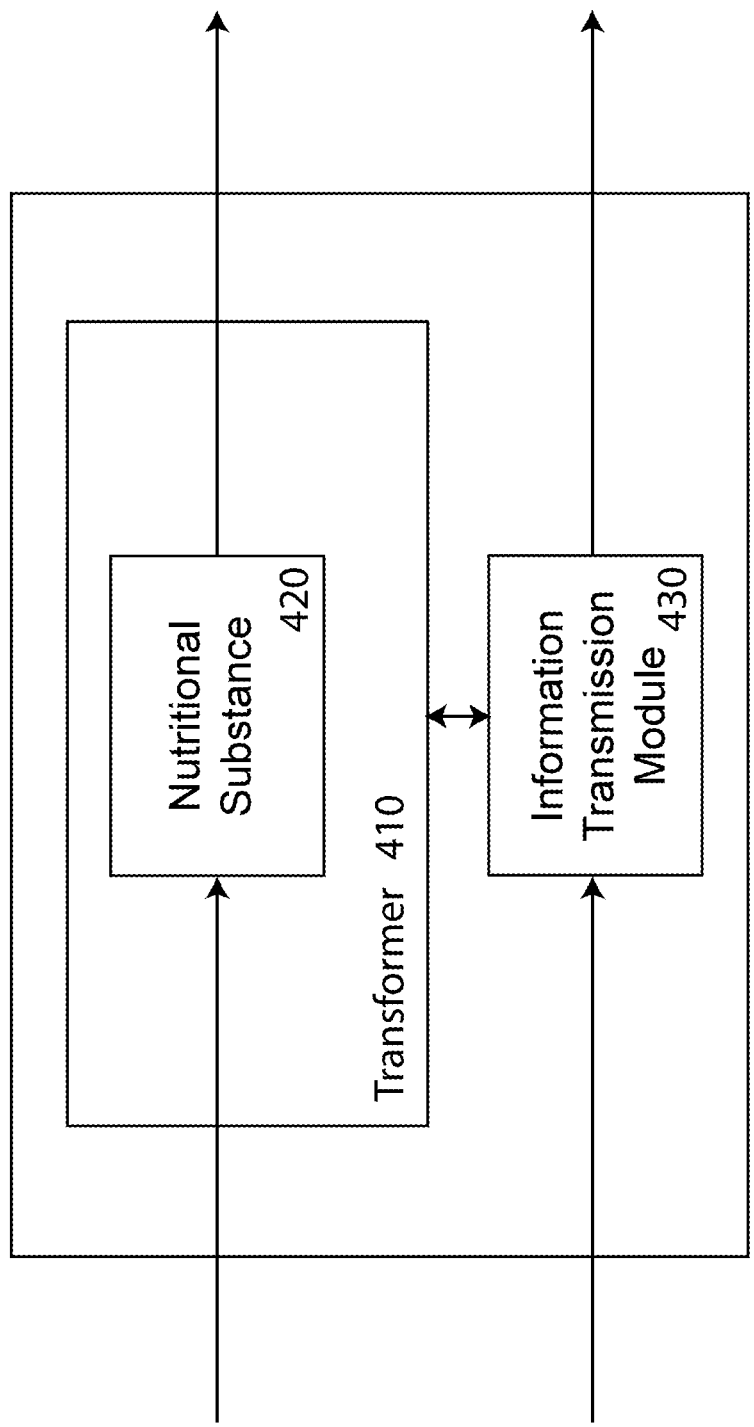
FIG. 4 shows a schematic functional block diagram of the transformation module 400 according to the present invention.

FIG. 4 shows an embodiment of transformation module 400 of the present invention. Transformation module 400 includes transformer 410, which acts upon nutritional substance 420, and information transmission module 430. When transformer 410 receives a nutritional substance 420, information transmission module 430 also receives, or retrieves information about the particular nutritional substance 420 that is to be transformed. This information can include creation information, packaging information, shipping information, and possibly previous transformation information. After nutritional substance 420 has been transformed by transformer 410, such information is passed along with the transformed nutritional substance 420 by the information transmission module 430, along with specific information relating to the transformation done by transformer 410.

For example, sweet corn that arrives for processing by transformer 410 has information associated with it, including the corn variety, where it was planted, when it was planted, when it was picked, the soil it was grown in, the water used for irrigation, and the fertilizers and pesticides that were used during its growth. There may also be information on nutritional, organoleptic and aesthetic values of the corn when it was preserved for shipment. This information may be stored in the labeling of the corn. However, it may be stored in a dynamic nutritional value database maintained by the grower, shipper, or the nutritional substances industry. Such information could be accessed by telecommunications systems, such as wireless telecommunication systems.

Additionally, the corn may have information associated with it regarding how it was preserved for shipment from the farm to transformation module 400. Such information may include historical information on the environment exterior the container it was shipped in, internal conditions of the container and actual information about the corn during the shipment. Additionally, if the preservation system acted upon such information in preserving the corn, information about the preservation measures may also be available. Such information may be stored in the preservation system. However, it may be stored in a dynamic nutritional value database maintained by the grower, shipper, or the nutritional substances industry. Such information could be accessed by means of telecommunications systems, such as wireless telecommunication systems.

In the example where the nutritional substance 420 is corn, transformer 410 removes the husk and the silk from the corn. It then separates the kernels from the cob, washes the kernels, and cooks them. Finally, transformer 410 packages the cooked corn in a can and labels the can.

During this transformation of the nutritional substance 420 by transformer 410, information about the transformation can be captured by transformer 410 and sent to information transmission module 430. This information can include how the transformation was accomplished; including information on the transformer used, the recipe implemented by transformer 410, and the settings for transformer 410 when the transformation occurred. Additionally, any information created during the transformation by transformer 410 can be sent to the information transmission module 430. This could include measured information, such as the actual cooking temperature, length of time of each of the steps. Additionally, this information could include measured aesthetic, organoleptic and nutritional values.

The dynamic label/information on the can may contain all the information provided to information transmission module 430. Preferably, this information is referenced by a dynamic information identifier which identifies the information regarding the corn in the can that is being transmitted by information transmission module 430.

In practice, information transmission module 430 would receive the information regarding the nutritional substance 420 from a database that is being used to track the corn during its journey from the farm to the consumer. When transformer 410 transforms nutritional substance 420, information transmission module 430 retrieves the appropriate information from the database, appends it with the information from transformer 410 regarding the transformation, and transmits it to another database. Alternatively, such information would be transmitted back to the original database, including the transformation information. Preferably, the information regarding the corn would simply be appended with the information from transformer 410 about the transformation. Such databases are individually and collectively referred to herein as a dynamic nutritional value database If the nutritional substance 420 can no longer be tracked by the reference information or a dynamic information identifier that accompanied the nutritional substance from the creator, then new reference information or a new dynamic information identifier may be created. For example, if the corn is combined with lima beans in the transformer 410, to make succotash, then the information for each may be combined and assigned a new reference number or a new dynamic information identifier. Preferably, a new entry is created in the dynamic nutritional value database, with references to the information related to the corn and the information related to the lima beans.

Figure 5:
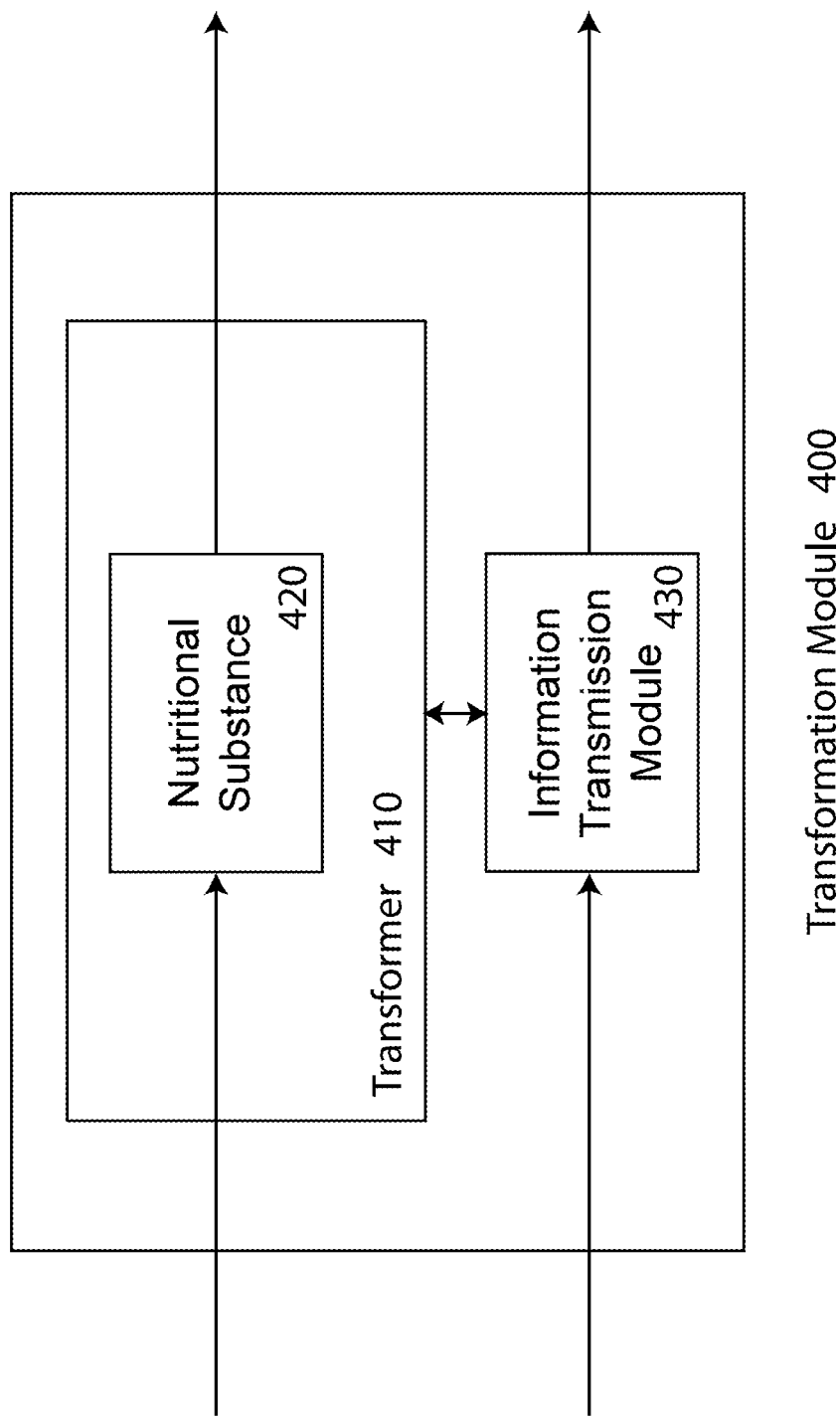
FIG. 5 shows a schematic functional block diagram of the transformation module 400 according to the present invention.

FIG. 5 shows an embodiment of transformation module 400 of the present invention. Transformation module 400 includes transformer 410, which acts upon nutritional substance 420, and information transmission module 430. When transformer 410 receives a nutritional substance 420, information transmission module 430 also receives, or retrieves information about the particular nutritional substance 420 that is to be transformed. This information can include creation information, packaging information, shipping information, and possibly previous transformation information. This information is used by transformer 410 to dynamically modify the transformation, the process referred to herein as adaptive transformation. After nutritional substance 420 has been transformed by transformer 410, such information is passed along with the transformed nutritional substance 420 by the information transmission module 430, along with specific information relating to the adaptive transformation done by transformer 410.

For example, sweet corn that arrives for processing by transformer 410 has origination information associated with it, including the corn variety, where it was planted, when it was planted, when it was picked, the soil it was grown in, the water used for irrigation, and the fertilizers and pesticides that were used during its growth. There may also be source information on nutritional, organoleptic and aesthetic values of the corn when it was preserved for shipment. This information may be stored in the labeling of the corn. However, it may be stored in a dynamic nutritional value database maintained by the grower, shipper, or the nutritional substances industry. Such information could be accessed by telecommunications systems, such as wireless telecommunication systems.

Additionally, the corn may have information associated with it regarding how it was preserved for shipment from the farm to transformation module 400. Such information may include historical information on the environment exterior the container it was shipped in, internal conditions of the container and actual information about the corn during the shipment. Additionally, if the preservation system acted upon such information in preserving the corn, information about the preservation measures may also be available. Such information may be stored in the preservation system. However, it may be stored in a database maintained by the grower, shipper, or the nutritional substances industry, also referred to herein as a dynamic nutritional value database. Such information could be accessed by means of telecommunications systems, such as wireless telecommunication systems.

Any, or all, of this information can be provided to transformer 410 by information transmission module 430. Transformer 410 can dynamically modify its transformation of nutritional substance 420 in response to such information to adaptively transform the nutritional substance in order to preserver or improve or minimize the degradation of the nutritional, organoleptic and/or aesthetic values of nutritional substance 420.

In the example where the nutritional substance 420 is corn, transformer 410 removes the husk and the silk from the corn. It then separates the kernels from the cob, washes the kernels, and cooks them. In response to the information provided by information transmission module 430, transformer can dynamically modify the cooking temperature and time. For example, if transformer 410 receives information that indicates that the corn is low in certain desirable nutrients, it might lower the cooking temperature and time to preserve those nutrients, thus achieving a more desirable nutritional value related to those specific nutrients in the transformed nutritional substance. However, if transformer 410 receives information that indicates that the corn is high in tough starches, it might raise the cooking temperature and time to soften the corn, thus achieving a more desirable organoleptic value related to the texture of the transformed nutritional substance. Finally, transformer 410 packages the cooked corn in a can and labels the can.

Additionally, transformer 410 can modify its transformation of the nutritional substance in response to measured attributes of the particular nutritional substance 420 being transformed. For example, transformer 410 can measure the color of the corn to be processed, and in response make adjustment to the transformation to preserve or enhance the color of the transformed corn, thus achieving a more desirable aesthetic value related to the appearance of the transformed nutritional substance.

During this adaptive transformation of the nutritional substance 420 by transformer 410, information about the transformation can be captured by transformer 410 and sent to information transmission module 430. This information can include how the transformation was accomplished; including information on any dynamic transformation modifications in response to information about the particular nutritional substance to be transformed, the recipe implemented by transformer 410, and the settings for transformer 410 when the transformation occurred. Additionally, any information created during the transformation by transformer 410 can be sent to the information transmission module 430. This could include measured information, such as the actual cooking temperature, length of time of each of the steps. Additionally, this information could include measured aesthetic, organoleptic, and nutritional information, weight, and physical dimension.

The label on the packaging may contain all the information provided to information transmission module 430. Preferably, this information is referenced by a dynamic information identifier which identifies the information regarding the nutritional substance in the packaging that is being transmitted by information transmission module 430.

In practice, information transmission module 430 would receive the information regarding the nutritional substance 420 from a database that is being used to track the corn during its journey from the farm to the consumer. When transformer 410 adaptively transforms nutritional substance 420, information transmission module 430 retrieves the appropriate information from the database, appends it with the information from transformer 410 regarding the adaptive transformation, and transmits it to another database. Alternatively, such information would be transmitted back to the original database, including the adaptive transformation information. Preferably, the information regarding the corn would simply be appended with the information from transformer 410 about the adaptive transformation. Such databases are individually and collectively referred to herein as a dynamic nutritional value database.

If the nutritional substance 420 can no longer be tracked by the reference information or dynamic information identifier that accompanied the nutritional substance from the creator, then new reference information or a new dynamic information identifier may be created. For example, if the corn is combined with lima beans in the transformer 410, to make succotash, then the information for each may be combined and assigned a new reference number or a new dynamic information identifier. Preferably, a new entry is created in the dynamic nutritional value database, with references to the information related to the corn and the information related to the lima beans.

The information system of the present invention can be utilized in such a way as to give nutritional substances a voice and allow consumers to listen to the nutritional substances, as will now be explained. Generally speaking, a tool, such as an application running on a smartphone or any other wireless device compatible with the application, can serve as the facilitator that provides nutritional substances with a voice and further allows the consumer to listen to the nutritional substance. For the purpose of discussion, such an application will be referred to herein as "Listen to your food." The consumer can use "Listen to your food" to query information-enabled nutritional substances regarding their compliance with input criteria chosen, selected, or provided by the consumer, or possibly provided by the application. "Listen to your food" further enables the communication of a simple response from the nutritional substance regarding the nutritional substance's compliance, or non-compliance, with the consumer's input criteria, and may further enable communication of dynamic pricing of the nutritional substance based on its residual nutritional, organoleptic, and/or aesthetic value.

As shown in FIG. 6 under the heading "Consumer Attribute Criteria Input", the consumer's detection and dynamic input criteria may include any number, from 0 to "n", and any combination of: component attributes (which include origin and creation information); integrity attributes; nutritional attributes; organoleptic attributes; and aesthetic attributes. Input criteria may exist as: one or more consumer profiles compatible with "Listen to your food"; component attributes; integrity attributes; nutritional attributes; organoleptic attributes; and aesthetic attributes chosen, selected, or input concurrently with the use of "Listen to your food"; or any combination thereof.

As shown in FIG. 6 under the headings ""Listen To Your Food" Compliance Response Format" and "Listen To Your Food" Non-compliance Response Format"", the simple response from the nutritional substance regarding the nutritional substance's compliance, or non-compliance, with the consumer's detection and dynamic input criteria may be provided in formats to be perceived by any one or more of auditory, visual, tactile, thermal, and olfactory mechanisms, and may be presented in a language format or a symbolic format. Such response would be provided through the consumer's smartphone, or any other wireless device compatible with "Listen to your food." It is preferred that the consumer can select, specify, or otherwise customize the mechanism and format of the response from the nutritional substance.

Audible responses regarding the consumer's detection and dynamic input criteria from the nutritional substance can be in the form of language, as indicated in FIG. 6 under the headings ""Listen To Your Food" Compliance Response Format"/"Audio"/"Language" and ""Listen To Your Food" Non-compliance Response Format"/"Audio"/"Language". It is understood that responses in the form of language could be provided in any language chosen by a consumer, or could be provided in a default language, such as the language spoken in the country of origin of the consumer's smartphone, or the language spoken in the current location of the smartphone. Any number of traditional responses communicating compliance or non-compliance with the consumer's input criteria may be utilized. Examples communicating compliance include, but are not limited to, audible statements of: "yes"; "affirmative", "good", "ok", and so forth. Examples communicating non-compliance include, but are not limited to, audible statements of: "no"; "stop", "bad", and so forth. Alternatively, "Listen to your food" may provide the consumer the ability to create custom audible language based responses, such as digital recordings stating "thumbs up" or "super" for compliance, or "forget about it" or "no way" for non-compliance. Further, audible language based responses might be selected by the consumer from libraries of digital recordings.

Audible responses regarding the consumer's detection and dynamic input criteria from the nutritional substance can be symbolic in form, as indicated in FIG. 6 under the headings ""Listen To Your Food" Compliance Response Format"/"Audio"/"Symbolic" and ""Listen To Your Food" Non-compliance Response Format"/"Audio"/"Symbolic". Any number of symbolic audible responses communicating compliance or non-compliance with the consumer's input criteria may be utilized. Examples communicating compliance include, but are not limited to: sounds associated with celebration, laughter, happy musical notes, and so forth. Examples communicating non-compliance include, but are not limited to: sound of tires skidding to a stop, sound of a frightened scream, sound of a railroad crossing, and so forth. "Listen to your food" may provide the consumer the ability to create custom audible symbolic responses, such as by making their own digital recordings. Further, audible symbolic responses might be chosen from libraries of digital recordings.

Visual responses regarding the consumer's detection and dynamic input criteria from the nutritional substance can be in the form of language, as indicated in FIG. 6 under the headings ""Listen To Your Food" Compliance Response Format"/"Visual"/"Language" and ""Listen To Your Food" Non-compliance Response Format"/"Visual"/"Language". It is understood that visual responses in the form of language could be provided in any language chosen by a consumer, or could be provided in a default language, such as the written language in the country of origin of the consumer's smartphone, or the written language in the current location of the smartphone. Any number of traditional responses communicating compliance or non-compliance with the consumer's input criteria may be utilized. Examples communicating compliance include, but are not limited to, written statements of: "yes"; "affirmative", "good", "ok", and so forth. Examples communicating non-compliance include, but are not limited to, written statements of: "no"; "stop", "bad", and so forth. Alternatively, "Listen to your food" may provide the consumer the ability to create custom visual language based responses, such as text stating "thumbs up" or "super" for compliance, or "forget about it" or "no way" for non-compliance. Further, visual language based responses might be selected by the consumer from libraries of text or text images.

Visual responses regarding the consumer's detection and dynamic input criteria from the nutritional substance can be symbolic in form, as indicated in FIG. 6 under the headings ""Listen To Your Food" Compliance Response Format"/"Visual"/"Symbolic" and ""Listen To Your Food" Non-compliance Response Format"/"Visual"/"Symbolic". Any number of symbolic visual responses communicating compliance or non-compliance with the consumer's input criteria may be utilized. Examples communicating compliance include, but are not limited to: a green light, image of a check-mark, image of a plus sign, and so forth. Examples communicating non-compliance include, but are not limited to: a red light, image of a skull and cross-bones, image of the "Ø" symbol, and so forth. "Listen to your food" may provide the consumer the ability to create custom visual symbolic responses, such as by making or capturing their own digital images. Further, visual symbolic responses might be chosen from libraries of digital images.

Tactile responses regarding the consumer's detection and dynamic input criteria from the nutritional substance can be symbolic in form, as indicated in FIG. 6 under the headings ""Listen To Your Food" Compliance Response Format/"Other sensory"/"Tactile" and ""Listen To Your Food" Non-compliance Response Format"/"Other sensory"/"Tactile". Any number of symbolic tactile responses communicating compliance or non-compliance with the consumer's input criteria may be utilized. Examples communicating compliance include, but are not limited to: vibration or pattern of vibration. Examples communicating non-compliance include, but are not limited to: no vibration, vibration or pattern of vibration different than that communicating compliance. "Listen to your food" may provide the consumer the ability to create custom tactile symbolic responses, or may allow tactile symbolic responses to be chosen from libraries of tactile responses.

Thermal responses regarding the consumer's detection and dynamic input criteria from the nutritional substance can be symbolic in form, as indicated in FIG. 6 under the headings ""Listen To Your Food" Compliance Response Format/"Other sensory"/"Thermal" and ""Listen To Your Food" Non-compliance Response Format"/"Other sensory"/"Thermal". A variety of symbolic thermal responses communicating compliance or non-compliance with the consumer's input criteria may be utilized. Examples communicating compliance include, but are not limited to: warm to the touch sensation. Examples communicating non-compliance include, but are not limited to: cold to the touch sensation. "Listen to your food" may provide the consumer the ability to create custom thermal symbolic responses, or may allow thermal symbolic responses to be chosen from libraries of thermal responses.

Olfactory responses regarding the consumer's detection and dynamic input criteria from the nutritional substance can be symbolic in form, as indicated in FIG. 6 under the headings ""Listen To Your Food" Compliance Response Format/"Other sensory"/"Olfactory" and ""Listen To Your Food" Non-compliance Response Format"/"Other sensory"/"Olfactory". Any number of symbolic olfactory responses communicating compliance or non-compliance with the consumer's input criteria may be utilized. Examples communicating compliance include, but are not limited to: a scent of candy, a scent of flowers, and so forth. Examples communicating non-compliance include, but are not limited to: a scent of something burned, a musty scent, and so forth. "Listen to your food" may provide the consumer the ability to create custom olfactory symbolic responses, or may allow olfactory symbolic responses to be chosen from libraries of olfactory responses Consumer input criteria regarding component attributes may include, but are not limited to, any combination of: specific ingredients (i.e., sugar, gluten, soy product, peanut product, and so forth); classes of nutritional substances (i.e., organic, vegan, free range, Kosher, and so forth); origin and creation of ingredients (i.e., country of origin, region of creation, food group, species, where it was transformed, how it was preserved, and so forth); additives (i.e., preservatives, accelerators, colorants, substitutes, and so forth) and any other type of attribute regarding the components of a nutritional substance. It is also understood that such criteria may be input to confirm or rule out any particular attribute. For example, input criteria regarding component attributes for a vegan consumer with a peanut allergy might include "vegan" and "no peanut products". Input criteria regarding component attributes for a British national who prefers to eat organic nutritional substances might include "country of origin UK" and "organic".

Consumer input criteria regarding component attributes may be provided by a consumer concurrent with his use of the "Listen to Your Food" application, prior to his use of the "Listen to Your Food" application (such as by a personal profile compatible with the application), or as a combination of both. For example, a consumer with an existing "Listen to Your Food" compatible profile may be on holiday in a particular region far from his home. His existing "Listen to Your Food" compatible profile may include no input criteria requiring, or limiting, "region of creation". The consumer wants to experience truly local cuisine, so he can instruct the "Listen to Your Food" application that his input criteria includes his existing profile plus an additional input criteria requiring that the "region of creation" is related to the specific region he is visiting. Further, he might instruct the application in this fashion every time he uses it while on holiday, or alternatively, he could instruct the application that his input criteria includes "region of creation" related to the particular region for a time period corresponding to his stay in the particular region. If the consumer was planning to visit several different regions far from his home during his holiday, he might instruct the application that his input criteria includes his existing profile plus an additional input criteria requiring that the "region of creation" is related to his current location for a time period corresponding to his holiday.

In another example, a consumer's "Listen to Your Food" compatible profile might include the aggregated input criteria corresponding to a particular group of consumers, such as his entire family. In this way, the consumer can simplify shopping for his entire family. Additionally, at any time the consumer might instruct the application that the input criteria includes the aggregate of any two or more individual or group profiles so that he may efficiently shop for those two or more individuals or groups. For example, a consumer may be preparing to go grocery shopping for his family and two dinner guests. One dinner guest has a peanut allergy and the other only eats organic food. The consumer can instruct the application that his input criteria includes a group profile corresponding to his family aggregated with the input profiles of his two guests. Alternatively, the consumer can instruct the application that his input criteria includes a group profile corresponding to his family aggregated with the additional input criteria of "no peanut product" and "organic". In this way, the consumer can utilize the "Listen to Your Food" application to efficiently meet the nutritional needs of his family and quests. It is understood that the input criteria regarding component attributes can include the aggregate of any combination of "Listen to Your Food" compatible individual profiles, group profiles, and additional specific input criteria.

Consumer input criteria regarding integrity attributes may include, but are not limited to, any combination of: specific substances related to creation (i.e., pesticides, fertilizers, hormones, water, and so forth); contamination (i.e., chemical, radiation, biological, heavy metals, radioactive isotopes, pollutants, and so forth); adulteration of any kind (i.e. spoilage, tampering, recall, loss of package integrity); and any other type of attribute regarding the integrity of the nutritional substance. It is also understood that such criteria may be input to confirm or eliminate any particular criteria. By way of example only, input criteria regarding integrity attributes for a consumer of shellfish might include "no heavy metals" and "no pesticides". Input criteria regarding integrity attributes for a consumer of chicken might include "no antibiotics" and "no artificial hormones". Input criteria regarding integrity attributes for a consumer of any packaged product might include "no tampering" or "no spoilage". The input criteria regarding integrity attributes could allow the consumer to verify the true nature of a nutritional substance, for example, if it is beef or horse meat.

It is understood that, similar to input criteria regarding component attributes, input criteria regarding integrity attributes may be provided by a consumer concurrent with his use of the "Listen to Your Food" application, prior to his use of the "Listen to Your Food" application (such as by a personal profile compatible with the application), or as a combination of both. It is further understood that the input criteria regarding integrity attributes can include the aggregate of any combination of "Listen to Your Food" compatible individual profiles, group profiles, and additional specific input criteria.

Consumer input criteria regarding nutritional attributes, wherein nutritional attributes comprise nutritional values and changes in nutritional values, may include, but are not limited to, any combination of: specific values and changes in values of vitamins (i.e., vitamin C content of orange juice); specific values and changes in values of probiotic content (i.e., level of active *lactobacillus* in yogurt); specific values and changes in values of fat content (i.e., fat content in ground meat); and any other type of nutritional attributes of a nutritional substance. It is also understood that such criteria may be input to confirm or eliminate any particular criteria. By way of example only, input criteria regarding nutritional attributes for a consumer of orange juice might include "vitamin C content≥75% vitamin C content of fresh orange juice". Input criteria regarding nutritional attributes for a consumer of ground beef might include "fat content≤7%".

It is understood that, similar to input criteria regarding component attributes, input criteria regarding nutritional attributes may be provided by a consumer concurrent with his use of the "Listen to Your Food" application, prior to his use of the "Listen to Your Food" application (such as by a personal profile compatible with the application), or as a combination of both. It is further understood that the input criteria regarding nutritional attributes can include the aggregate of any combination of "Listen to Your Food" compatible individual profiles, group profiles, and additional specific input criteria.

Consumer input criteria regarding organoleptic attributes, wherein organoleptic attributes comprise organoleptic values and changes in organoleptic values, may include, but are not limited to, any combination of: specific values and changes in values of flavor (i.e. tannin levels in wine change with time and storage conditions and greatly affect the flavor of the wine); specific values and changes in values of aroma (i.e. the aroma of cinnamon is a value directly related to the aroma and flavor of the cinnamon); specific values and changes in values of ripeness (i.e. ripeness of tomatoes changes with time and conditions and is a value directly related to the texture and flavor of tomatoes); and any other type of organoleptic attribute of a nutritional substance. It is also understood that such criteria may be input to confirm or eliminate any particular criteria. By way of example only, input criteria regarding organoleptic attributes for a consumer of wine might include a specified "acceptable range for tannins". Input criteria regarding organoleptic attributes for a consumer of cinnamon might include a specified "acceptable level of aroma". Input criteria regarding organoleptic attributes for a consumer of tomatoes might include "ripeness 100%±10%".

It is understood that, similar to input criteria regarding component attributes, input criteria regarding organoleptic attributes may be provided by a consumer concurrent with his use of the "Listen to Your Food" application, prior to his use of the "Listen to Your Food" application (such as by a personal profile compatible with the application), or as a combination of both. It is further understood that the input criteria regarding organoleptic attributes can include the aggregate of any combination of "Listen to Your Food" compatible individual profiles, group profiles, and additional specific input criteria.

Consumer input criteria regarding aesthetic attributes, wherein aesthetic attributes comprise aesthetic values and changes in aesthetic values, may include, but are not limited to, any combination of: specific values and changes in values of color of nutritional substances, such as: those occurring as a result of oxidation (i.e. oxidation induced changes in color of sliced apples, guacamole, meat, and so forth); those occurring as a result of maturation (i.e., cherries, tomatoes and so forth); those occurring as a result of cooking (i.e., steamed shrimp, tuna, and so forth); and any other type of aesthetic attribute of a nutritional substance. It is also understood that such criteria may be input to confirm or eliminate any particular criteria. By way of example only, input criteria regarding aesthetic attributes for a consumer of beef might include "very red", which further corresponds to a visual scale available through "Listen to Your Food". Input criteria regarding aesthetic attributes for a consumer of cherries might include "medium red", which further corresponds to a visual scale available through "Listen to Your Food". Input criteria regarding aesthetic attributes for a consumer of steamed shrimp might include "light to dark pink", which further corresponds to a visual scale available through "Listen to Your Food". It is also understood that other aesthetic attributes including, but not limited to, visual texture, shape, size, and so forth may be specified.

It is understood that, similar to input criteria regarding component attributes, input criteria regarding aesthetic attributes may be provided by a consumer concurrent with his use of the "Listen to Your Food" application, prior to his use of the "Listen to Your Food" application (such as by a personal profile compatible with the application), or as a combination of both. It is further understood that the input criteria regarding aesthetic attributes can include the aggregate of any combination of "Listen to Your Food" compatible individual profiles, group profiles, and additional specific input criteria.

Examples of a consumer utilizing "Listen to Your Food" are now provided.

In one example, a consumer uses "Listen to Your Food" on his smartphone to determine nutritional substance compliance or non-compliance with his need for Gluten free nutritional substances, and further to determine compliance or non-compliance with his aversion to eating horse meat, as he is an avid equestrian and believes horses are too noble to be eaten. He goes to the supermarket and opens the "Listen to Your Food" application on his smartphone. The application asks him to identify the specific consumer profiles and the specific input criteria with which he would like to determine compliance, or non-compliance, of nutritional substances. He has never created a consumer profile compatible with "Listen to Your Food", so he uses the application to enter the input criteria "no Gluten" and "no horse meat". Because he has never created a consumer profile, the application asks him to select or create the customized notification mechanism and format for "compliance" and "non-compliance", or to select the defaults provided by the application. He accepts the application's default settings regarding notification mechanism and format for "compliance" and "non-compliance", which are: image of a green traffic light and audible "YES" for Compliance; and image of a red traffic light and audible "NO" for Non-compliance. He proceeds to do his grocery shopping, and he scans the dynamic information identifier on the first item that he considers for purchase with the camera on his smartphone. "Listen to Your Food" directs the smartphone to retrieve from the information module the information regarding Gluten content and horse meat content of the nutritional substance referenced by the dynamic information identifier. The information retrieved indicates that this first item does not contain horse meat, but does contain Gluten. "Listen to Your Food" directs the smartphone to display an image of a red traffic light and play an audible "NO". The consumer knows immediately that the first item does not meet his needs. He scans the dynamic information identifier on a second item that he considers for purchase with the camera on his smartphone. "Listen to Your Food" directs the smartphone to retrieve from the information module the information regarding Gluten content and horse meat content of the nutritional substance referenced by the dynamic information identifier of the just scanned second item. The information retrieved indicates that this second item does not contain Gluten, but does contain horse meat additives. "Listen to Your Food" directs the smartphone to display an image of a red traffic light and play an audible "NO". The consumer knows immediately that the second item does not meet his needs. He selects a third item and scans its dynamic information identifier with his smartphone. "Listen to Your Food" directs the smartphone to retrieve from the information module the information regarding Gluten content and horse meat content of the nutritional substance referenced by the dynamic information identifier of the just scanned third item. The information retrieved indicates that this third item contains no Gluten and no horse meat. "Listen to Your Food" directs the smartphone to display an image of a green traffic light and play an audible "YES". The consumer knows immediately that the third item meets his needs. In addition to informing the consumer that the third item meets his needs, "Listen to your food" can also communicate dynamically determined pricing, wherein the price of the third item is determined, preferably by the information module, as a function of its residual nutritional, organoleptic, and/or aesthetic value. It is understood that such a dynamically determined price may additionally, or alternatively, be communicated by the supermarket, such as by using the "Listen to your food" application at the display case where the third item is displayed, or at the checkout stand In another example, a consumer uses "Listen to Your Food" on his smartphone to determine nutritional substance compliance or non-compliance with his needs. He goes to the supermarket and opens the "Listen to Your Food" application on his smartphone. The application asks him to identify the specific consumer profiles and the specific input criteria with which he would like to determine compliance, or non-compliance, of nutritional substances. He has used the application before, and had previously created a consumer profile by following the application's prompts to enter his input criteria. He selects his personal profile, which requires foods rich in vitamin C and the probiotic *lactobacillus*, and additionally non-adulterated product. The personal profile he created for himself includes the input criteria for orange juice: "vitamin C content≥75% of fresh", for yogurt: "*lactobacillus* level≥50% of fresh", and for all nutritional substances: "non-adulterated". His personal profile further includes his custom settings regarding notification mechanism and format for "compliance" and "non-compliance", which are: image of a thumbs-up and audible sound of a crowd cheering for Compliance; and image of a thumbs-down and audible sound of a crowd booing for Non-compliance. He proceeds to do his grocery shopping, and he scans the dynamic information identifier on a carton of orange juice with the camera on his smartphone. "Listen to Your Food" directs the smartphone to retrieve from the information module the information regarding vitamin C content and adulteration of the orange juice referenced by that dynamic information identifier. The information retrieved indicates that this particular orange juice has lost 40% of its fresh vitamin C content, and is non-adulterated. "Listen to Your Food" accordingly directs the smartphone to display a thumbs-down and audible sound of a crowd booing. The consumer knows immediately that this item does not meet his needs. He selects an alternate orange juice and scans its dynamic information identifier with his smartphone. "Listen to Your Food" directs the smartphone to retrieve from the information module the information regarding vitamin C content and adulteration of the orange juice referenced by the dynamic information identifier of the just scanned alternate item. The information retrieved indicates that this alternate item has only lost 15% of its fresh vitamin C content, and is non-adulterated. "Listen to Your Food" directs the smartphone to display a thumbs-up and audible sound of a crowd cheering. The consumer knows immediately that the alternate item meets his needs. In addition to informing the consumer that the orange juice meets his needs, "Listen to your food" can also communicate dynamically determined pricing, wherein the price of the orange juice is determined, preferably by the information module, as a function of its residual nutritional, organoleptic, and/or aesthetic value. It is understood that such a dynamically determined price may additionally, or alternatively, be communicated by the supermarket, such as by using the "Listen to your food" application at the display case where the orange juice is displayed, or at the checkout stand.

The consumer now scans the dynamic information identifier on a container of yogurt with the camera on his smartphone. "Listen to Your Food" directs the smartphone to retrieve from the information module the information regarding *lactobacillus* content and adulteration of the yogurt referenced by that dynamic information identifier. The information retrieved indicates that this particular yogurt has lost only 20% of its fresh *lactobacillus* content, but is adulterated. "Listen to Your Food" accordingly directs the smartphone to display a thumbs-down and audible sound of a crowd booing. The consumer knows immediately that this item does not meet his needs. He selects an alternate yogurt and scans the dynamic information identifier on a container of yogurt with the camera on his smartphone. "Listen to Your Food" directs the smartphone to retrieve from the information module the information regarding *lactobacillus* content and adulteration of the yogurt referenced by that dynamic information identifier. The information retrieved indicates that this particular yogurt is non-adulterated, but has lost 90% of its fresh *lactobacillus* content. "Listen to Your Food" accordingly directs the smartphone to display a thumbs-down and audible sound of a crowd booing. The consumer knows immediately that this item does not meet his needs. He selects yet another yogurt and scans the dynamic information identifier on a container of yogurt with the camera on his smartphone. "Listen to Your Food" directs the smartphone to retrieve from the information module the information regarding *lactobacillus* content and adulteration of the yogurt referenced by the dynamic information identifier of the just scanned item. The information retrieved indicates that this yogurt has only lost 15% of its fresh *lactobacillus* content, and is non-adulterated. "Listen to Your Food" directs the smartphone to display a thumbs-up and audible sound of a crowd cheering. The consumer knows immediately that this item meets his needs. In addition to informing the consumer that the yogurt meets his needs, "Listen to your food" can also provide dynamically determined pricing, wherein the price of the yogurt is determined as a function of its residual nutritional, organoleptic, and/or aesthetic value. It is understood that such a dynamically determined price may additionally, or alternatively, be determined by the supermarket, such as by using the "Listen to your food" application at the display case where the yogurt is displayed, or at the checkout stand In another example, a consumer uses "Listen to Your Food" on his smartphone to determine nutritional substance compliance, or non-compliance, with his needs, which include going to the supermarket to shop for himself, his spouse, and a breakfast guest. At the supermarket, he opens the "Listen to Your Food" application on his smartphone. The application asks him to identify the specific consumer profiles and the specific input criteria with which he would like to determine compliance, or non-compliance, of nutritional substances. He and his spouse have used the application before, and have each previously created their own consumer profile by following the application's prompts to enter their individual input criteria. The breakfast guest has not previously created a consumer profile for "Listen to Your Food". The consumer selects his personal profile, which requires foods rich in vitamin C, and selects the personal profile of his spouse, which includes foods high in the probiotic *lactobacillus*, and while he does not have a personal profile for the breakfast guest, he knows that the quest believes in eating foods that are organic and unadulterated. The personal profile he created for himself includes the input criteria for orange juice: "vitamin C content≥75% of fresh". His personal profile further includes his custom settings regarding notification mechanism and format for "compliance" and "non-compliance", which are: image of a thumbs-up and audible sound of a crowd cheering for Compliance; and image of a thumbs-down and audible sound of a crowd booing for Non-compliance. His spouse's personal profile includes the input criteria for yogurt: "*lactobacillus* level≥50% of fresh". He instructs "Listen to Your Food" to use an aggregated input criteria comprising his personal profile plus his spouse's personal profile plus, in order to account for the breakfast guest's preferences, the added input criteria of: all nutritional substances "organic creation" and all nutritional substances: "non-adulterated". He further instructs the application to use his custom settings regarding notification mechanism and format for "compliance" and "non-compliance". He proceeds to do his grocery shopping, and he scans the dynamic information identifier on a carton of orange juice with the camera on his smartphone. "Listen to Your Food" directs the smartphone to retrieve from the information module the information regarding the vitamin C content, organic creation, and adulteration of the orange juice referenced by that dynamic information identifier. The information retrieved indicates that this particular orange juice has lost 20% of its fresh vitamin C content, is non-adulterated, but was squeezed from genetically altered oranges, which are not considered organic. "Listen to Your Food" accordingly directs the smartphone to display a thumbs-down and audible sound of a crowd booing. The consumer knows immediately that this item does not meet his needs. He selects an alternate orange juice and scans its dynamic information identifier with his smartphone. "Listen to Your Food" directs the smartphone to retrieve from the information module the information regarding vitamin C content, organic creation, and adulteration of the orange juice referenced by the dynamic information identifier of the just scanned alternate item. The information retrieved indicates that this alternate item has lost 15% of its fresh vitamin C content, was organically created, and is non-adulterated. "Listen to Your Food" directs the smartphone to display a thumbs-up and audible sound of a crowd cheering. The consumer knows immediately that this item meets his needs. "Listen to your food" can also provide dynamically determined pricing, wherein the price of the orange juice is determined as a function of its residual nutritional, organoleptic, and/or aesthetic value. Such a dynamically determined price may additionally, or alternatively, be determined by the supermarket, such as by using the "Listen to your food" application at the display case where the orange juice is displayed, or at the checkout stand.

The consumer now scans the dynamic information identifier on a container of yogurt with the camera on his smartphone. "Listen to Your Food" directs the smartphone to retrieve from the information module the information regarding *lactobacillus* content, organic creation, and adulteration of the yogurt referenced by that dynamic information identifier. The information retrieved indicates that this particular yogurt has lost only 20% of its fresh *lactobacillus* content, is non-adulterated, but was made with milk from cows who's diet included antibiotics and hormones, which means that the yogurt is not organic. "Listen to Your Food" accordingly directs the smartphone to display a thumbs-down and audible sound of a crowd booing. The consumer knows immediately that this item does not meet his needs. He selects an alternate yogurt and scans the dynamic information identifier on the container of yogurt with the camera on his smartphone. "Listen to Your Food" directs the smartphone to retrieve from the information module the information regarding *lactobacillus* content, organic creation, and adulteration of the yogurt referenced by that dynamic information identifier. The information retrieved indicates that this particular yogurt is non-adulterated, but has lost 90% of its fresh *lactobacillus* content. "Listen to Your Food" accordingly directs the smartphone to display a thumbs-down and audible sound of a crowd booing. The consumer knows immediately that this item does not meet his needs. He selects yet another container of yogurt and scans the dynamic information identifier on the container of yogurt with the camera on his smartphone. "Listen to Your Food" directs the smartphone to retrieve from the information module the information regarding *lactobacillus* content, organic creation, and adulteration of the yogurt referenced by the dynamic information identifier of the just scanned item. The information retrieved indicates that this yogurt has only lost 15% of its fresh *lactobacillus* content, was organically created, and is non-adulterated. "Listen to Your Food" directs the smartphone to display a thumbs-up and audible sound of a crowd cheering. The consumer knows immediately that this item meets his needs. "Listen to your food" can also provide dynamically determined pricing, wherein the price of the yogurt is determined as a function of its residual nutritional, organoleptic, and/or aesthetic value. Such a dynamically determined price may additionally, or alternatively, be determined by the supermarket, such as by using the "Listen to your food" application at the display case where the yogurt is displayed, or at the checkout stand To illustrate other benefits of the present invention the following example is provided of a consumer who is faced with making a purchasing decision based on several variables. A consumer would like to make an Italian entrée for dinner on Friday, but must go to the market on Monday (4 days in advance of preparing the entrée), and is not sure of an appropriate recipe to meet his unique needs, for example, nutritional substances low in sodium, gluten-free and high in lycopene. The consumer uses his smartphone to: access a nutritional substance information module that has access to a consumer module with the consumer's personal consumer profile, including low sodium, gluten-free and high lycopene preferences, and retrieves appropriate recipes; or alternatively, the consumer might use his smartphone to access various recipe databases for Italian recipes using an application on his smartphone to filter the recipes according to his consumer profile, including low sodium, gluten-free and high lycopene; or alternatively, the consumer might use his smartphone to access a recipe database for Italian recipes wherein the database provides consumer interface through the consumer's smartphone screen to provide input regarding the consumer's needs, such as low sodium, gluten-free and high lycopene. In this way, the consumer obtains a recipe comprising a list of ingredients for an entrée that meets his essential health needs, and can capture the recipe. In this case, the consumer has selected a recipe for gluten-free pasta with marinara sauce.

The consumer then uses his smartphone, tablet computer, or personal computer to locate nearby supermarkets and verify if the supermarkets have all of the required ingredients to make the desired gluten-free pasta with marinara sauce, plus other items he needs to purchase, such as a specific bottle of wine and cheese to enjoy with the entrée. Unfortunately, all of the ingredients and other items are not available at his preferred supermarket, but he finds that they are available at an alternate supermarket nearby. He is not familiar with the alternate supermarket, and does not know the locations of the various ingredients or the other items in the unfamiliar supermarket, so in order to make his shopping experience more efficient he uses his smartphone, tablet computer, or personal computer to request the location of the ingredients and other items within the supermarket and the fastest route within the supermarket to collect the items on his shopping list. For example, the consumer's smartphone utilizes an application created for the alternate supermarket to identify the location within the alternate supermarket of the various items on his shopping list and generate a route within the alternate supermarket that the consumer can follow that will result in the least amount of time required for collecting the ingredients. The suggested route may instruct that he starts in the produce isle of the supermarket, in this case isle number 1, and provide the list of ingredients to collect at that location. As he collects the various ingredients required from the produce isle, his smartphone can allow him to delete a collected item, change its status to indicate it has been collected, or may allow him to move it from a list of items to be collected to a list of items collected. Upon collecting the last item from the produce isle, the smartphone instructs him to go to the specific isle where the low sodium, gluten-free pasta can be found, which in this case is isle 11. Upon collecting the gluten-free pasta from isle 11, the smartphone instructs him to go to the specific isle where wine is located, which in this case is isle 14. Upon collecting the wine from isle 14, the smartphone instructs him to go to the specific isle where cheese can be found, in this case isle 15. In this way, the consumer's time spent locating and collecting the items required for purchase is minimized because he is able to make one quick pass through the supermarket, visiting only the correct location for each item, and with no backtracking Additionally, his smartphone can easily verify that all required items have been collected. Further, the "Listen to your food" application on his smartphone can be used to quickly determine compliance, or non-compliance, of each item with the nutritional substance needs that he has communicated through his "Listen to your food" profile or input criteria. Preferably, the nutritional substance is provided with a QR code including the dynamic information identifier and a URL to hardlink the consumer to the nutritional substance information module. Using the "Listen to your food" application, the consumer could use his smartphone to scan such a QR code on a nutritional substance of interest. The smartphone, would then hardlink the consumer to the nutritional substance information system, retrieve source and $\Delta N$ information associated with the dynamic information identifier, determine compliance, or non-compliance with the consumer's needs, and communicate the compliance or non-compliance. "Listen to your food" can also provide dynamically determined pricing, wherein the price of the nutritional substance is determined as a function of its residual nutritional, organoleptic, and/or aesthetic value. Such a dynamically determined price may additionally, or alternatively, be determined by the supermarket, such as by using the "Listen to your food" application at the display case where the nutritional substance is displayed, or at the checkout stand If no single supermarket has all of the ingredients and other items are required, the consumer can still retrieve a route requiring the least time to collect the items from multiple supermarkets. For example, if the consumer must visit two supermarkets to collect all items, the route retrieved can include both the driving instructions from the consumer's home to a first supermarket, the route to follow within the first supermarket, driving instructions from the first supermarket to a second supermarket, the route to follow within the second supermarket, and driving instructions from the second supermarket to the consumer's home. Further, his smartphone can be used to retrieve a dynamic information identifier from any nutritional substance provided with a dynamic information identifier and a URL to hardlink to the nutritional substance information module so that he may utilize the "Listen to your food" application to quickly determine the nutritional substance's compliance, or non-compliance, with his needs, and may further determine its dynamic pricing, wherein its dynamic pricing is a function of its residual nutritional, organoleptic, and/or aesthetic value.

The consumer goes to the supermarket to purchase the ingredients for the desired entrée. The consumer is interested in preparing a meal that meets his needs when it is prepared 4 days from the time of purchase. The recipe calls for tomatoes and pasta among the ingredients. Using the "Listen to your food" application, the consumer scans a dynamic information identifier on Heirloom tomatoes with his smartphone, such as by scanning a QR code including the dynamic information identifier and a URL to hardlink to the nutritional substance information module, to determine if the Heirloom tomatoes are in compliance, or non-compliance, with his needs for high lycopene when prepared in 4 days. Based upon their current nutritional value and the $\Delta N$ associated with 4 days storage at expected storage conditions, "Listen to your food" determines that they do not comply, and communicates their non-compliance through the smartphone. The consumer decides to check if Roma tomatoes will meet his needs. Using the "Listen to your food" application, the consumer scans a dynamic information identifier on Roma tomatoes with his smartphone, such as by scanning a QR code including the dynamic information identifier and a URL to hardlink to the nutritional substance information module and access the dynamic nutritional value database. Based upon their current nutritional value and the $\Delta N$ associated with 4 days storage at expected storage conditions, the application determines that the Roma tomatoes will meet his high lycopene needs when prepared in 4 days from now, and communicates their compliance through the smartphone. In a similar fashion, the consumer scans a QR code including a dynamic information identifier and URL for the nutritional substance information module on one or more pasta products, to determine if they are in compliance, or non-compliance, with his low sodium and gluten-free needs when prepared in 4 days, and makes purchasing decisions regarding pasta based upon the indication of compliance or non-compliance provided through his smartphone. The consumer is not the only entity that has benefited from the dynamic nutritional information about the Heirloom tomatoes, the Roma tomatoes and the pasta, as data regarding the consumer's needs for low sodium, gluten-free, and high lycopene can be collected by the consumer module and correlated with the respective dynamic information identifiers, and are available to, such as transmitted to, the information module and are of particular interest and accessible to the growers and packagers of the respective tomatoes and to the transformer of the one or more pastas. The dynamic nutritional value database can provide source information and $\Delta N$ information of how the nutritional values of any other ingredients he is buying have evolved thus far, and will evolve during the next 4 days (tomatoes, pasta, garlic, onions, basil etc. . . . ) if those ingredients are supplied with dynamic information identifiers, and may further determine its dynamic pricing, wherein its dynamic pricing is a function of its residual nutritional, organoleptic, and/or aesthetic value. This consumer information can be saved and be made available to all other entities in the nutritional substance supply system.

Also, while shopping for the ingredients for the pasta with marinara sauce, the consumer decides to buy a bottle of wine and some cheese to go with the meal. Using the "Listen to your food" application, the consumer uses his smartphone to scan QR codes (providing dynamic information identifiers and URL to hardlink to the nutritional substance information module) form bottles of wine and cheeses he is considering for purchase. Source and $\Delta N$ information referenced to the dynamic information identifier of each product scanned is retrieved from the dynamic nutritional value database, and determinations are made regarding compliance, or non-compliance, in 4 days, with the consumer's needs regarding maturity of nutritional substances that actually discompose to be ready to eat or drink, like the cheese and the bottle of wine. The determination of compliance or non-compliance is communicated through the consumer's smartphone. In addition, the consumer's smartphone may provide dynamically determined pricing, wherein the dynamically determined pricing is a function of the nutritional substances residual nutritional, organoleptic, and/or aesthetic value.

It is understood that consumers will also benefit from all the functionalities of the present inventions regarding monitoring the consumption of medicaments. For example, preventing them from taking medicaments that have expired, lost their effectiveness, are contraindicated based on concurrent use of other medicaments, contain specific allergens, and so forth.

According to other embodiments, preservation systems of the present invention enable a nutritional substance to interact and communicate with its preservation system in a dynamic manner through the natural changes $\Delta N$ it experiences, and further enable the preservation system to convey information associated with those changes to the consumer. As used herein, preservation systems may include, but are not limited to, any internal or external portion of a nutritional substance package, container, carton, bottle, carton, box, bag, vessel, cup, plate, wrapper, label, or any other apparatus used to preserve, store, transfer, present, or serve a nutritional substance.

An example of the present invention is provided of bottled wine interacting, or communicating, with a portion of its container. As the wine in the container ages it naturally experiences many changes $\Delta N$, including changes in acidity, tannin content, gas emission, sugar content, alcohol content, and others. According to the present invention, a cork, a cap, a submerged coupon or indicator, or any part of the surface of the bottle can monitor one or more $\Delta N$ and convey to a consumer the $\Delta N$, or a corresponding current state, of the wine at any moment the consumer wants to know, such as when he is deciding to purchase or open the container. In addition, the $\Delta N$ information conveyed may be related to, or associated with, pricing of the bottled wine For example, if the $\Delta N$ reflects that the wine is immature, its pricing may be slightly reduced, as compared to its pricing when the $\Delta N$ reflects that the wine is mature. If the $\Delta N$ reflects that the wine is overly mature, and therefore less desirable than when mature, the pricing may be more significantly reduced, depending on the extent of its over maturity.

In another example, a milk carton containing milk could have a small area on its side with encapsulated gel in direct contact with the milk. As the milk ages, its bacteria count naturally increases, also resulting in a reduced ph. The bacteria will be able to penetrate the gel and the gel will gradually change color in response to the increasing bacteria content or concentration, indicating the increase in bacteria within the milk, and therefore a current state of the milk. For example, the gel may change from green, wherein green represents an acceptable bacteria level and associated shelf life, to yellow, wherein yellow represents a higher acceptable bacteria level and associated shorter shelf life, to red, wherein red represents the milk has an unacceptably high bacteria level and is not apt for drinking any more. The message conveyed by the changing color of the gel may also be related to dynamic pricing of the milk, for instance, milk cartons having green gel being associated with a higher price than milk having yellow gel.

Alternatively, the gel may gradually change color in response to a reduction in ph, wherein changes in ph are surrogates for changes in bacteria levels. As the milk ages, its bacteria count naturally increases, reducing its ph. For example, the gel may change from green, wherein green represents a ph level corresponding to an acceptable bacteria level and associated shelf life, to yellow, wherein yellow represents a lower ph level and corresponding higher acceptable bacteria level and associated shorter shelf life, to red, wherein red represents a still lower ph and corresponding unacceptably high bacteria level and is not apt for drinking any more. The message conveyed by the changing color of the gel may additionally be related to dynamic pricing of the milk, for instance, milk cartons having green gel being associated with a higher price than milk having yellow gel.

It is understood that nutritional substances, as used herein, includes, but is not limited to, synthetic compounds such as medicaments, supplements, and other substances intended for consumption or introduction into a consumer. The present invention may include embodiments wherein a portion of the nutritional substance interacting or communicating with its container is segregated from a portion of the nutritional substance to be consumed. This would be of particular benefit for packaged goods including synthetic compounds such as medicaments, in which case it would be desirable to segregate the portion of medicament interacting or communicating with the container from the portion of the medicament for consumption. In this case, the portion of the medicament interacting or communicating with the container would serve as a parallel sample of the medicament provided for consumption. This might be accomplished by providing a separate, permanently sealed cavity on or within the medicament container, its cover, its label, or any permanently sealed cavity structure known in the art, wherein the structure contains the portion of medicament intended to interact or communicate with the container. The permanently sealed cavity can interact with the portion of medicament communicating with it to convey desired ΔN information regarding the medicament. Such ΔN information may be associated with a degradation of the medicament, a residual nutritional or medicinal value of the medicament, an expiration date of the medicament, utilized in any other way to ensure the medicament's safety and efficacy when a consumer uses it, and could even be utilized to dynamically determine its pricing.

Other examples of the present invention could include, but are not limited to, containers like jars, glasses, or cups that could detect when there is an unhealthy level of toxins, antibiotics, fungus, bacteria, pesticides, or other undesirable components in tap water intended for consumption, or if the coffee poured into a cup has caffeine or not. The principle at work is that of symbiosis, similar to that which occurs between a banana and its peel. The banana peel has a natural evolution from green to black that conveys the level of maturity of the banana. The peel reacts to the natural ΔN that occurs during the banana's maturation process, wherein the ΔNs may include changes in acidity, sugar content, and bacteria level. The ΔNs of the banana independently and collectively have an effect on the aesthetic values of the banana peel, which in turn conveys to the consumer when and how the banana may best be consumed. For example, a green peel indicates that the banana is not yet ripe and should not be eaten. Yellow indicates that it may be suitable for consumption, but will not be very sweet. Yellow with a few black spots indicates that it is suitable for consumption, and will be sweat. Mostly black indicates that it is suitable for use in baked goods or to be fried. Very black indicates that it is no longer suitable for consumption. In this same manner when the peel has been punctured or torn and the maturating process is accelerated as more oxygen than normal contacts the banana, the banana peel quickly turns black alerting the consumer. Therefore the consumer does not have to rely on a static expiration date to determine the banana's suitability for consumption.

Unless the context clearly requires otherwise, throughout the description and the claims, the words "comprise," "comprising," and the like are to be construed in an inclusive sense (i.e., to say, in the sense of "including, but not limited to"), as opposed to an exclusive or exhaustive sense. As used herein, the terms "connected," "coupled," or any variant thereof means any connection or coupling, either direct or indirect, between two or more elements. Such a coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the invention is not intended to be exhaustive or to limit the invention to the precise form disclosed above. While specific examples for the invention are described above for illustrative purposes, various equivalent modifications are possible within the scope of the invention, as those skilled in the relevant art will recognize. While processes or blocks are presented in a given order in this application, alternative implementations may perform routines having steps performed in a different order, or employ systems having blocks in a different order. Some processes or blocks may be deleted, moved, added, subdivided, combined, and/or modified to provide alternative or sub-combinations. Also, while processes or blocks are at times shown as being performed in series, these processes or blocks may instead be performed or implemented in parallel, or may be performed at different times. Further any specific numbers noted herein are only examples. It is understood that alternative implementations may employ differing values or ranges.

The various illustrations and teachings provided herein can also be applied to systems other than the system described above. The elements and acts of the various examples described above can be combined to provide further implementations of the invention.

Any patents and applications and other references noted above, including any that may be listed in accompanying filing papers, are incorporated herein by reference. Aspects of the invention can be modified, if necessary, to employ the systems, functions, and concepts included in such references to provide further implementations of the invention.

These and other changes can be made to the invention in light of the above Detailed Description. While the above description describes certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

While certain aspects of the invention are presented below in certain claim forms, the applicant contemplates the various aspects of the invention in any number of claim forms. For example, while only one aspect of the invention is recited as a means-plus-function claim under 35 U.S.C. §112, sixth paragraph, other aspects may likewise be embodied as a means-plus-function claim, or in other forms, such as being embodied in a computer-readable medium. Any claims intended to be treated under 35 U.S.C. §112, ¶6 will begin with the words "means for." Accordingly, the applicant reserves the right to add additional claims after filing the application to pursue such additional claim forms for other aspects of the invention.

I claim:

1. A system for creating adaptively transformed nutritional substances comprising:
    a dynamic information identifier associated with at least one component of a single or multiple component nutritional substance, wherein
    the dynamic information identifier allows retrieval of source information for the component nutritional substance associated with it, wherein
    said source information comprises dynamically generated information reflecting a state or change in state of the component nutritional substance prior to adaptive transformation;
    a transformer for adaptive transformation of said single or multiple component nutritional substances with processing parameters responsive to said source information to create an adaptively transformed nutritional substance; and
    a dynamic nutritional value database for storage of said source information and information related to said adaptive transformation, said dynamic nutritional value database containing information regarding a $\Delta N$, and pricing information, value or data derived or estimated using said $\Delta N$, wherein $\Delta N$ is a change in a nutritional, organoleptic, or aesthetic value of one or more component nutritional substances.

2. A system for creating adaptively transformed nutritional substances according to claim 1 wherein:
    said processing parameters are adapted to said source information for optimization of a desired property of the adaptively transformed nutritional substance.

3. A system for creating adaptively transformed nutritional substances according to claim 1 wherein:
    said processing parameters are adapted to said source information for optimization of a desired property of one or more of said component nutritional substances.

4. A system for creating adaptively transformed nutritional substances according to claim 1 further comprising:
    a dynamic information identifier associated with the adaptively transformed nutritional substance allowing retrieval of said source information or information related to said adaptive transformation or said $\Delta N$, or pricing information, value or data derived or estimated using said $\Delta N$.

5. A system for creating adaptively transformed nutritional substances according to claim 1 wherein:
    said source information further comprises information demonstrating origination or content of one or more of said component nutritional substances.

6. A system for creating adaptively transformed nutritional substances according to claim 1 wherein:
    one or more of said component nutritional substances has been previously preserved, packaged or transformed.

7. A system for creating adaptively transformed nutritional substances according to claim 6 wherein:
    said source information further comprises information demonstrating origination or content of one or more of said previously preserved, packaged or transformed component nutritional substances.

8. A system for creating adaptively transformed nutritional substances according to claim 1 further comprising:
    a device for retrieval of said source information using the dynamic information identifier.

9. A system for creating adaptively transformed nutritional substances according to claim 1 further comprising:
    a device for retrieval of said source information or information related to said adaptive transformation using a dynamic information identifier associated with the adaptively transformed nutritional substance.

10. A system for creating adaptively transformed nutritional substances from one or more component nutritional substances, the system comprising:
    a dynamic information identifier associated with each component nutritional substance for allowing retrieval of dynamically generated source information for the component nutritional substances,
    source information comprising at least one of a nutritional value, an organoleptic value, or an aesthetic value of the component nutritional substance; and
    a transformer for adaptive transformation of said component nutritional substances with processing parameters responsive to said source information for improvement, maintenance, or minimization of degradation of the nutritional value, the organoleptic value, or the aesthetic value of one or more component nutritional substances following adaptive transformation,
    wherein said dynamically generated source information is useful for indicating a $\Delta N$, and pricing information, value or data associated with the $\Delta N$, and wherein the $\Delta N$ is a change in a nutritional, organoleptic, or aesthetic value of one or more component nutritional substances occurring prior to said adaptive transformation; said change comprising any of a maintenance, improvement, degradation or expiration.

11. A system for creating adaptively transformed nutritional substances from one or more component nutritional substances according to claim 10 wherein:
the dynamic information identifier associated with one or more component nutritional substances further allows retrieval of information demonstrating origination or content of said component nutritional substance.

12. A system for creating adaptively transformed nutritional substances from one or more component nutritional substances according to claim 10 wherein:
one or more of said component nutritional substances has been previously preserved, packaged or transformed.

13. A system for creating adaptively transformed nutritional substances from one or more component nutritional substances according to claim 10 wherein:
source information for said previously preserved, packaged, or transformed component nutritional substances is useful for indicating a $\Delta N$, and pricing information, value or data associated with the $\Delta N$, and wherein $\Delta N$ is a change in a nutritional, organoleptic, or aesthetic value of said previously preserved, packaged or transformed component nutritional substance occurring prior to said adaptive transformation; and
the dynamic information identifier associated with said previously preserved, packaged or transformed component nutritional substance further allows retrieval of information demonstrating origination or content of said previously preserved, packaged or transformed component nutritional substance.

14. A system for creating adaptively transformed nutritional substances from one or more component nutritional substances according to claim 10 further comprising:
a dynamic nutritional value table for presentation of information derived from said dynamically generated source information or information related to said improvement, maintenance, or minimization of degradation; wherein said presentation of information comprises a $\Delta N$, and pricing information, value or data associated with the $\Delta N$, and wherein $\Delta N$ is a change in a nutritional, organoleptic, or aesthetic value of one or more component nutritional substances.

15. A system for creating adaptively transformed nutritional substances from one or more component nutritional substances according to claim 10 further comprising:
a dynamic information identifier associated with the adaptively transformed nutritional substance allowing retrieval of said dynamically generated source information or information related to said improvement, maintenance, or minimization of degradation;
the information available for retrieval comprising a $\Delta N$, and pricing information, value or data derived or estimated using a $\Delta N$, wherein $\Delta N$ is a change in a nutritional, organoleptic, or aesthetic value of one or more component nutritional substances.

16. A system for creating adaptively transformed nutritional substances from one or more component nutritional substances according to claim 10 further comprising:
a device for retrieval of said dynamically generated source information or a related $\Delta N$, price, value, or information demonstrating origination or content, using the dynamic information identifier associated with each component nutritional substance.

17. A system for creating adaptively transformed nutritional substances from one or more component nutritional substances according to claim 15 further comprising:
a device for retrieval of the information using the dynamic information identifier associated with the adaptively transformed nutritional substance.

18. A system for creating adaptively transformed nutritional substances from one or more component nutritional substances according to claim 17, wherein:
said device comprises a nutritional substance conditioner.

19. A system for generating a dynamic nutritional value table for a nutritional substance comprising:
a device for accessing and storing source information for the nutritional substance, and
subsequent information for the nutritional substance, said subsequent information having been dynamically ascertained by at least one of a measurement of the nutritional substance or preservation information related to the nutritional substance or transformation information related to the nutritional substance; and
a dynamic nutritional value table generated from said source information and said subsequent information about the nutritional substance, and including a $\Delta N$ and price or value indicated by a $\Delta N$, wherein $\Delta N$ is a change in a nutritional, organoleptic, or aesthetic value of the nutritional substance and said change comprises any of a maintenance, improvement, degradation or expiration date.

20. A system for generating a dynamic nutritional value table for a nutritional substance according to claim 19 wherein:
said source information comprises source information for multiple component nutritional substances;
said dynamic nutritional value table comprises the $\Delta N$ or price or value information indicated by the $\Delta N$ for said multiple component nutritional substances.

21. A system for generating a dynamic nutritional value table for a nutritional substance according to claim 20 wherein:
one or more of said component nutritional substances has been previously preserved, packaged or transformed;
thereby changing the $\Delta N$ or price or value information indicated by the $\Delta N$ for said previously preserved, packaged or transformed component nutritional substance.

22. A system for generating a dynamic nutritional value table for a nutritional substance according to claim 19, wherein:
said nutritional substance comprises one or more component nutritional substances, said component nutritional substances having been, or
not having been, previously preserved, packaged or transformed; and
said source information further demonstrates origination or content of one or more of said component nutritional substances.

23. A system for generating a dynamic nutritional value table for a nutritional substance according to claim 19 further comprising:
a dynamic information identifier for accessing the dynamic nutritional value table or for accessing said source information and said subsequent information from which the dynamic nutritional value table can be indicated.

24. A system for generating a dynamic nutritional value table for a nutritional substance according to claim 19 wherein:
said $\Delta N$ or information indicated by said $\Delta N$ presented by the dynamic nutritional value table indicates one or more of a nutritional value, an organoleptic value, an aesthetic value, a price or value, or expiration date of the nutritional substance.

25. A system for generating a dynamic nutritional value table for a nutritional substance according to claim 19 wherein:

said ΔN or information indicated by said ΔN presented by the dynamic nutritional value table indicates a best consumption date of the nutritional substance.

26. A system for generating a dynamic nutritional value table for a nutritional substance according to claim 19 wherein:

said ΔN or information indicated by said ΔN presented by the dynamic nutritional value table indicates a perceived qualitative value of the nutritional substance.

27. A system for generating a dynamic nutritional value table for a nutritional substance according to claim 20 further comprising:

using the ΔN or information indicated by the ΔN for said multiple component nutritional substances to indicate a rate of loss of a nutritional value, an organoleptic value, an aesthetic value, an expiration date, or price of said multiple component nutritional substances.

28. A system for generating a dynamic nutritional value table for a nutritional substance according to claim 19 wherein:

the dynamic nutritional value table indicates compliance with a predetermined consumer profile or current consumer query.

29. A method of dynamically valuing or pricing a nutritional substance comprising:

accessing source information for the nutritional substance;

accessing subsequent information for the nutritional substance, said subsequent information having been dynamically ascertained by at least one of a measurement of the nutritional substance or preservation information related to the nutritional substance or transformation information related to the nutritional substance; and making use of said source information and said subsequent information to generate a dynamic nutritional value table of information about the nutritional substance;

said information for communicating a ΔN, and price or value indicated by the ΔN, wherein ΔN is a change in a nutritional, organoleptic, or aesthetic value of the nutritional substance and said change comprises any of a maintenance, improvement, or degradation.

30. A method of generating a dynamic nutritional value table for a nutritional substance comprising:

accessing source information for the nutritional substance; and accessing subsequent information for the nutritional substance, said subsequent information having been dynamically ascertained by at least one of a measurement of the nutritional substance or preservation information related to the nutritional substance or transformation information related to the nutritional substance; and making use of said source information and said subsequent information to generate a dynamic nutritional value table for presentation of information about the nutritional substance;

said presentation of information for communicating a ΔN or information indicated by a ΔN, wherein ΔN is a change in a nutritional, organoleptic, or aesthetic value of the nutritional substance and said change comprises any of a maintenance, improvement, degradation, or expiration.

\* \* \* \* \*